(12) United States Patent
Boyajian et al.

(10) Patent No.: US 11,904,180 B2
(45) Date of Patent: Feb. 20, 2024

(54) ADJUSTABLE ILLUMINATORS AND METHODS FOR PHOTODYNAMIC THERAPY AND DIAGNOSIS

(71) Applicant: DUSA Pharmaceuticals, Inc., Wilmington, MA (US)

(72) Inventors: Thomas Boyajian, Wilmington, MA (US); Mark Carota, Chelmsford, MA (US); Brian Mazejka, Salem, NH (US); Michael Leccese, North Andover, MA (US)

(73) Assignee: DUSA Pharmaceuticals, Inc., Wilmington, MA (US)

( * ) Notice: Subject to any disclaimer, the term of this patent is extended or adjusted under 35 U.S.C. 154(b) by 226 days.

(21) Appl. No.: 16/808,631

(22) Filed: Mar. 4, 2020

(65) Prior Publication Data

US 2020/0269063 A1     Aug. 27, 2020

Related U.S. Application Data

(60) Division of application No. 15/487,991, filed on Apr. 14, 2017, now Pat. No. 10,603,508, which is a
(Continued)

(51) Int. Cl.
*A61N 5/06*     (2006.01)
*A61B 5/00*     (2006.01)

(52) U.S. Cl.
CPC ............ *A61N 5/062* (2013.01); *A61B 5/0064* (2013.01); *A61B 5/0082* (2013.01);
(Continued)

(58) Field of Classification Search
CPC ................. A61N 5/062; A61N 5/0616; A61N 2005/0642; A61N 2005/0626;
(Continued)

(56) References Cited

U.S. PATENT DOCUMENTS 4,667,658 A    5/1987   Guibert
5,032,400 A    7/1991   Wiersum et al.
(Continued)

FOREIGN PATENT DOCUMENTS

CA          2568744 A1    12/2005
CA          2738861 A1     7/2011
(Continued)

OTHER PUBLICATIONS

Willey et al., "Temperature-Modulated Photodynamic Therapy for the Treatment of Actinic Keratosis on the Extremities: A Pilot Study" Dermatol Surg 2014;40:1094-1102, Oct. 1, 2014 (Year: 2044).*
(Continued)

*Primary Examiner* — Boniface N Nganga
(74) *Attorney, Agent, or Firm* — Foley & Lardner LLP

(57) ABSTRACT

An illuminator for photodynamically diagnosing or treating a surface includes a plurality of panels. The illuminator further includes a plurality of light sources, each mounted to one of the plurality of panels. The plurality of light sources are configured to irradiate the surface with substantially uniform intensity visible light. The illuminator also includes a heat source configured to emit heat to a patient. The heat increases the generation of a photoactivatable agent and thus shortens the time needed to complete photodynamic therapy.

7 Claims, 16 Drawing Sheets

Related U.S. Application Data continuation-in-part of application No. 15/292,731, filed on Oct. 13, 2016, now Pat. No. 10,589,122.

(60) Provisional application No. 62/241,902, filed on Oct. 15, 2015.

(52) U.S. Cl.
CPC .... *A61N 5/0616* (2013.01); *A61N 2005/0626* (2013.01); *A61N 2005/0633* (2013.01); *A61N 2005/0642* (2013.01); *A61N 2005/0651* (2013.01); *A61N 2005/0652* (2013.01); *A61N 2005/0662* (2013.01); *A61N 2005/0663* (2013.01)

(58) Field of Classification Search
CPC .... A61N 2005/0633; A61N 2005/0651; A61N 2005/0652; A61N 2005/0662; A61N 2005/0663

See application file for complete search history.

(56) References Cited

U.S. PATENT DOCUMENTS

| | | |
|---|---|---|
| 5,211,938 A | 5/1993 | Kennedy et al. |
| 5,601,838 A | 2/1997 | Hind |
| 5,686,065 A | 11/1997 | Haney |
| 5,814,008 A | 9/1998 | Chen et al. |
| 5,849,027 A | 12/1998 | Gart et al. |
| 6,223,071 B1 | 4/2001 | Lundahl et al. |
| 6,559,183 B1 | 5/2003 | Schmid et al. |
| 6,709,446 B2 | 3/2004 | Lundahl et al. |
| 6,897,238 B2 | 5/2005 | Anderson |
| 7,033,381 B1* | 4/2006 | Larsen ................ A61N 5/0616 607/90 |
| 7,156,865 B2 | 1/2007 | Waldmann |
| 7,190,109 B2 | 3/2007 | Lundahl et al. |
| 7,723,910 B2 | 5/2010 | Lundahl et al. |
| 7,730,893 B2 | 6/2010 | Dougal |
| 8,030,836 B2 | 10/2011 | Lundahl et al. |
| 8,216,289 B2 | 7/2012 | Lundahl et al. |
| 8,226,289 B2 | 7/2012 | Lindeberg |
| 8,758,418 B2 | 6/2014 | Lundahl et al. |
| 8,759,396 B2 | 6/2014 | Wulf et al. |
| 9,108,045 B2 | 8/2015 | Sakamoto et al. |
| 9,227,082 B2 | 1/2016 | McDaniel |
| 9,533,170 B2 | 1/2017 | Dye et al. |
| 9,597,150 B2 | 3/2017 | Lundahl |
| 10,357,567 B1 | 7/2019 | Lundahl et al. |
| 10,603,508 B2* | 3/2020 | Boyajian ............... A61B 5/0082 |
| 10,814,114 B2 | 10/2020 | Boyajian et al. |
| 11,135,293 B2 | 10/2021 | Lundahl et al. |
| 11,235,169 B1 | 2/2022 | Osterloh et al. |
| 2001/0021812 A1 | 9/2001 | Lundahl et al. |
| 2003/0088296 A1 | 5/2003 | Waldmann |
| 2003/0216795 A1 | 11/2003 | Harth et al. |
| 2004/0010299 A1 | 1/2004 | Tolkoff et al. |
| 2004/0143308 A1* | 7/2004 | Lundahl ............... A61N 5/0616 607/91 |
| 2004/0162596 A1 | 8/2004 | Altshuler et al. |
| 2004/0260365 A1 | 12/2004 | Groseth et al. |
| 2005/0075703 A1 | 4/2005 | Larsen |
| 2005/0090877 A1 | 4/2005 | Harth et al. |
| 2006/0182790 A1 | 8/2006 | Mayoral |
| 2006/0241726 A1 | 10/2006 | Whitehurst |
| 2006/0253175 A1 | 11/2006 | Fan et al. |
| 2006/0287696 A1 | 12/2006 | Wright et al. |
| 2007/0283655 A1 | 12/2007 | Tobin |
| 2008/0031924 A1 | 2/2008 | Gilson et al. |
| 2008/0188558 A1 | 8/2008 | Godal et al. |
| 2009/0247932 A1 | 10/2009 | Barolet |
| 2009/0324727 A1 | 12/2009 | Foguet Roca |
| 2010/0010591 A1 | 1/2010 | Daffer |
| 2010/0174222 A1* | 7/2010 | McDaniel ............. A61B 18/203 604/20 |
| 2010/0174223 A1 | 7/2010 | Sakamoto et al. |
| 2010/0179469 A1* | 7/2010 | Hammond ........... A61N 5/0624 604/20 |
| 2010/0298758 A1 | 11/2010 | Christiansen et al. |
| 2011/0020441 A1 | 1/2011 | Klaveness et al. |
| 2011/0053965 A1 | 3/2011 | Trigiante |
| 2011/0106222 A1 | 5/2011 | Wilson et al. |
| 2011/0224598 A1* | 9/2011 | Barolet ................ A61N 5/0616 604/20 |
| 2011/0293528 A1 | 12/2011 | Godal et al. |
| 2012/0283328 A1 | 11/2012 | Modi |
| 2012/0287671 A1 | 11/2012 | Parker et al. |
| 2013/0066404 A1 | 3/2013 | Tapper et al. |
| 2013/0190845 A1 | 7/2013 | Liu et al. |
| 2013/0274834 A1* | 10/2013 | Barolet ................ A61N 5/0616 607/88 |
| 2013/0289089 A1 | 10/2013 | Morris et al. |
| 2013/0304019 A1 | 11/2013 | Cooper et al. |
| 2013/0315999 A1 | 11/2013 | Paithankar et al. |
| 2014/0010761 A1 | 1/2014 | Parent et al. |
| 2014/0067024 A1* | 3/2014 | Jones ................... A61N 5/0616 607/90 |
| 2014/0121631 A1 | 5/2014 | Bean et al. |
| 2015/0162109 A1 | 6/2015 | Nager |
| 2015/0238776 A1 | 8/2015 | Sakamoto et al. |
| 2015/0290028 A1 | 10/2015 | Isserow et al. |
| 2015/0290470 A1* | 10/2015 | Tapper ................ A61N 5/0616 607/91 |
| 2016/0008623 A1 | 1/2016 | Jones et al. |
| 2016/0045757 A1 | 2/2016 | Groseth |
| 2016/0166846 A1 | 6/2016 | Chae |
| 2016/0346392 A1 | 12/2016 | Wulf |
| 2018/0344852 A1 | 12/2018 | Solioz et al. |
| 2019/0216927 A1 | 7/2019 | Lundahl et al. |
| 2019/0290763 A1 | 9/2019 | Lundahl et al. |
| 2020/0100997 A1 | 4/2020 | Soler et al. |
| 2020/0246630 A1 | 8/2020 | Boyajian et al. |
| 2020/0261580 A1 | 8/2020 | Willey |
| 2020/0398071 A1 | 12/2020 | Boyajian et al. |

FOREIGN PATENT DOCUMENTS

| | | | |
|---|---|---|---|
| DE | 69827286 T2 | 11/2005 | |
| EP | 1 238 652 A1 | 9/2002 | |
| EP | 1 311 259 B1 | 5/2003 | |
| EP | 3 143 986 A1 | 3/2017 | |
| JP | H04-500770 A | 2/1992 | |
| JP | 2002-529495 A | 9/2002 | |
| JP | 2010-513363 | 4/2010 | |
| JP | 2010-515714 A | 5/2010 | |
| KR | 20120100861 A * | 9/2012 | |
| WO | WO-93/09847 A1 | 5/1993 | |
| WO | WO-95/07077 A1 | 9/1993 | |
| WO | WO-96/06602 A1 | 3/1996 | |
| WO | WO-99/22802 A1 | 5/1999 | |
| WO | WO-02/13788 A1 | 2/2002 | |
| WO | WO-2007/112427 A2 | 10/2007 | |
| WO | WO-2009/003173 A1 | 12/2008 | |
| WO | WO-2009003173 A1 * | 12/2008 | ......... A61K 41/0057 |
| WO | WO-2009/074811 A2 | 6/2009 | |
| WO | WO-2011/124912 A1 | 10/2011 | |
| WO | WO-2013110021 A1 * | 7/2013 | ......... A61B 5/0064 |
| WO | WO-2014/131115 A1 | 9/2014 | |
| WO | WO-2015/041919 A1 | 3/2015 | |
| WO | WO-2019/018408 A1 | 1/2019 | |

OTHER PUBLICATIONS

Mordon S, A commentary on the role of skin temperature on the effectiveness of ALA-PDT in Dermatology, Photodiagnosis and Photodynamic Therapy, (Year: 2014).*

Braathen, Lasse R., et al. "Guidelines on the Use of Photodynamic Therapy for Nonmelanoma Skin Cancer: an International Consensus." Journal of the American Academy of Dermatology 56.1, Jan. 2007, pp. 125-143.

Dragieva, G. et al., "A Randomized Controlled Clinical Trial of Topical Photodynamic Therapy with Methyl Aminolaevulinate in

(56) References Cited

OTHER PUBLICATIONS the Treatment of Actinic Keratoses in Transplant Recipients." British Journal of Dermatology 151.1, Jul. 2004, pp. 196-200.
Kurwa, Habib A., et al., "A Randomized Paired Comparison of Photodynamic Therapy and Topical 5-Fluorouracil in the Treatment of Actinic Keratoses." Journal of the American Academy of Dermatology 41.3, Sep. 1999, pp. 414-418.
MacCormack, Mollie A., "Photodynamic Therapy in Dermatology: An Update on Applications and Outcomes." Seminars in Cutaneous Medicine and Surgery. vol. 27, No. 1, WB Saunders, Mar. 2008, pp. 52-62.
Ozog, David M., et al., "Photodynamic Therapy: A Clinical Consensus Guide." Dermatologic Surgery 42.7, Jul. 2016, pp. 804-827.
Wolf, Peter, et al., "Topical Photodynamic Therapy With Endogenous Porphyrins After Application of 5-Aminolevulinic Acid: An Alternative Treatment Modality for Solar Keratoses, Superficial Squamous Cell Carcinomas, and Basal Cell Carcinomas?" Journal of the American Academy of Dermatology 28.1, Jan. 1993, pp. 17-21.
Extended European Search Report, Application No. 20214586.8, dated Jun. 2, 2021, 8 pages.
USPTO Notice of Allowance, U.S. Appl. No. 16/438,702, dated May 20, 2021, 10 pages.
U.S. Appl. No. 17/487,698, filed Sep. 28, 2021, Lundahl et al.
U.S. Appl. No. 17/506,849, filed Oct. 21, 2021, Boyajian et al.
Affidavit of Duncan Hall, Aug. 10, 2021.
Agostinis et al. Photodynamic therapy of cancer: an update. CA: A Cancer Journal for Clinicians. May 2011; 61(4):250-2.
Aktilite CL128 Operators Manual with Metvixia, Revised 2008.
Ameluz, Prescribing Information (2016).
Berardesca E, Vignoli GP, Fideli D, Maibach H. Effect of occlusive dressings on the stratum corneum water holding capacity. The American Journal of the Medical Sciences. Jul. 1992;304(1):25-28.
Bissonnette R. Photodynamic therapy. In: Gold M.H., editor. Photodynamic Therapy in Dermatology. Springer Science and Business Media, LLC; New York, NY, USA: 2011. pp. 221-229.
Blu-U, Operating Manual (2006).
Calderhead RG. Light-emitting diode phototherapy in dermatological practice in lasers in dermatology and medicine. Lasers in Dermatology and Medicine. Aug. 2011:231-265.
CV of Dr. Howard Rogers MD, PhD.
Declaration of Dr. Howard Rogers MD, PhD, Oct. 19, 2021.
DUSA Levulan Press Release, Dec. 6, 1999.
European Medicines Agency CHMP Assessment Report (excerpts), Oct. 20, 2011.
Fauteck Europe PMC Website Database Listing, Oct. 25, 2007.
Fauteck JD, Ackermann G, Birkel M, Breuer M, Moor AC, Ebeling A, Ortland C. Fluorescence characteristics and pharmacokinetic properties of a novel self-adhesive 5-ALA patch for photodynamic therapy of actinic keratoses, 2008.
Harris DR. Percutaneous absorption and the surface area of occluded skin: a scanning electron microscopic study. British Journal of Dermatology. 1974; 91(27-32).
Hongcharu W., Taylor C., Chang, Y., Aghasi, D., Suthamjariya, K., Anderson, R. Topical ALA-photodynamic therapy for the treatment of acne vulgaris. J Invest Dermatol. Aug. 2000;115(2):183-92.
International Patent Reviews, LLC review of U.S. Pat. No. 10,357,567 dated Jul. 26, 2021.
Jeffes E., McCullough J., Weinstein G., Fergin P., Nelson J., Shull T., Simpson K., Bukaty L., Hoffman W., Fong N. Photodynamic therapy of actinic keratosis with topical 5-aminolevulinic acid. A pilot dose-ranging study. Arch Dermatol. 1997.
Levulan, Label (2002).
Levulan, Label (2009).
MacCormack MA. Photodynamic therapy in dermatology: an update on applications and outcomes. Semin Cutan Med Surg. Mar. 2008;27(1):52-62.
McLaren G. Photodynamic therapy. In; Pfenninger and Fowler's procedures for primary care. Third Ed. Mosby Elsevier; Philadelphia, PA: 2011. pp. 397-400.
News article entitled DUSA Pharmaceuticals To Pay U.S. $20.75 Million To Settle False Claims Act Allegations Relating To Promotion Of Unsupported Drug Administration Process, Aug. 24, 2020.
Ozog, D., Rkein, A., Fabi, S., Gold M., Goldman, M., Lowe, N., Martin, G., Munavalli, G. Photodynamic therapy: A clinical consensus guide. Dermatol Surg. Jul. 2016;42(7):804-27.
Palm M., Goldman PM. Aminolevulinic acid: actinic keratosis and photorejuvenation. In: Gold M.H., editor. Photodynamic Therapy in Dermatology. Springer Science and Business Media, LLC. Nov. 2011:5-30.
Petition for Inter Partes Review Under 35 U.S.C. 312, Oct. 19, 2021.
Rick K, Sroka R, Stepp H, Kriegmair M, Huber RM, Jacob K, Baumgartner R. Pharmacokinetics of 5-aminolevulinic acidinduced protoporphyrin IX in skin and blood. J Photochem Photobiol B. Oct. 1997;40(3):313-9.
Sakamoto FH, Torezan L, Anderson RR. Photodynamic therapy for acne vulgaris: a critical review from basics to clinical practice: part II. Understanding parameters for acne treatment with photodynamic therapy. J Am Acad Dermatol. Aug. 2010;63(2):195-211.
Sotiriou E, Apalla Z, Maliamani F, Zaparas N, Panagiotidou D, Ioannides D. Intraindividual, right-left comparison of topical 5-aminolevulinic acid photodynamic therapy vs. 5% imiquimod cream for actinic keratoses on the upper extremities, 2009.
Sotiriou Pubmed Website Database Listing, Sep. 23, 2009.
USPTO Office Action, U.S. Appl. No. 16/791,004, dated Oct. 25, 2021, 26 pages.
Wachowska et al., Aminolevulinic acid (ALA) as a prodrug in photodynamic therapy of cancer. Molecules. May 2011; 16(5): 4140-4164.
Willey A, Anderson RR, Sakamoto FH. Temperature-modulated photodynamic therapy for the treatment of actinic keratosis on the extremities. Dermatologic Surgery. Oct. 2014;40(10):1094-1102.
Willey Pubmed Website Database Listing, Oct. 2014.
Wolf P., Rieger E. and Kerl H. Topical photodynamic therapy with endogenous porphyrins after application of 5-aminolevulinic acid: an alternative treatment modality for solar keratoses, superficial squamous cell carcinomas, and basal cell carcinomas?, Jan. 1993.
Australian Examination Report, Application No. 2020267186, dated Nov. 19, 2021,6 pages.
USPTO Office Action, U.S. Appl. No. 17/487,698, dated Dec. 17, 2021, 21 pages.
Zhang et al., "Topical 5-Aminolevulinic Photodynamic Therapy with Red Light vs Intense Pulsed Light for the Treatment of Acne Vulgaris _ A Spilit Face, Randomized, Prospective Study," Dermato-Endocrinology, 2018, vol. 9, No. 1, e1375634 (9 pages).
USPTO Notice of Allowance, U.S. Appl. No. 16/438,702, dated Mar. 22, 2021, 14 pages.
USPTO Office Action, U.S. Appl. No. 17/009,871, dated Mar. 23, 2021, 9 pages.
USPTO Office Action, U.S. Appl. No. 17/109,311, dated Mar. 2, 2021, 16 pages.
USPTO Office Action, U.S. Appl. No. 16/438,702, dated Oct. 13, 2020, 17 pages.
Australian Office Action, Application No. 2019200152, dated Nov. 11, 2019, 9 pages.
European Office Action, Application No. 16787667.1, dated Sep. 24, 2019, 5 pages.
GLAD.com.au: "GLAD History", 2012, [online] URL: http://www.glad.com.au/about-glad/glad-history/, retrieved online Nov. 8, 2019.
Herschel S. Zackheim et al., Topical Corticosteroids for Mycosis Fungoides, Experience in 79 Patients, Arch Dermatol, Aug. 1998, vol. 134, pp. 949-954.
International Preliminary Report on Patentability, PCT/US2016/056572, dated Apr. 26, 2018, 9 pages.
International Preliminary Report on Patentability, PCT/US2018/027070, dated Oct. 24, 2019, 10 pages.
International Search Report and Written Opinion International Application No. PCT/US2018/027070, dated Oct. 16, 2018, 18 pages.
Notice of Allowance, U.S. Appl. No. 15/487,991, dated Oct. 2, 2019, 16 pages.
Partial International Search, Annex to Form PCT/ISA/206, International Application No. PCT/US2018/027070, dated Jul. 19, 2018, 10 pages.

(56) References Cited

OTHER PUBLICATIONS

USPTO Advisory Action, U.S. Appl. No. 15/487,991, dated May 15, 2018, 5 pages.
USPTO Interview Summary, U.S. Appl. No. 15/487,991, dated Sep. 22, 2017, 4 pages.
USPTO Notice of Allowance, U.S. Appl. No. 15/292,731, dated Nov. 14, 2019, 12 pages.
International Search Report, International Application No. PCT/US2018/042505, dated Oct. 2, 2018, 2 pages.
Andrea Willey, Introducing the New Red Light ALA PDT, Feb. 15, 2017, 3 pages, https://andreawilleymd.com/the-new-red-light-ala-pdt/.
Andrea Willey et al., Abstract of Temperature-Modulated Photodynamic Therapy for the Treatment of Actinic Keratosis on the Extremities: A Pilot Study, Dermatol Surg., 40 (10), Oct. 2014, 2 pages, https://www.ncbi.nlm.nih.gov/pubmed/25207759.
Dermatology Times, Warming the Skin During PDT Incubation Period Boosts Porphyrin Synthesis, Apr. 1, 2013, 3 pages.
USPTO Notice of Allowance, U.S. Appl. No. 17/009,871, dated Jul. 22, 2021, 14 pages.
USPTO Notice of Allowance, U.S. Appl. No. 17/109,311, dated Aug. 10, 2021, 14 pages.
USPTO Office Action, U.S. Appl. No. 17/109,311, dated Jul. 20, 2021, 17 pages.
USPTO Office Action, U.S. Appl. No. 17/009,871, dated Dec. 2, 2020, 15 pages.
Britannica, The Editors of Encyclopaedia, "Gel: Physics and Chemistry", 4 pages, Jul. 20, 1998, and "Gel: Additional Information", 1 page, Available on line at: https://www.britannica.com/science/gel and https://www.britannica.com/science/gel/additional-info#history.
Fehr et al., Photodynamic Therapy of Vulvar and Vaginal Condyloma and Intraepithelial Neoplasia Using Topically Applied 5-Aminolevulinic Acid, Lasers in Surgery and Medicine, 2002, 30:273-279, 7 pages.
Fehr et al., Selective Photosensitizer Distribution in Vulvar Condyloma Acuminatum After Topical Application of 5-Aminolevulinic Acid, Am. J. Obstet. Gynecol., vol. 174(3), Mar. 1996, pp. 951-957.
Hurlimann et al., Photodynamic Therapy of Superficial Basal Cell Carcinomas Using Topical 5-Aminolevulinic Acid in a Nanocolloid Lotion, Pharmacology and Treatment, Dermatology 197, 1998, pp. 248-254.
Reinhold et al., A Randomized, Double-Blind, Phase III, Multicentre Study to Evaluate the Safety and Efficacy of BF-200 ALA (AmeluzR) vs. Placebo in the Field-Directed Treatment of Mild-to-Moderate Actinic Keratosis with Photodynamic Therapy (PDT) When Using the BF-RhodoLED® Lamp, British Journal of Dermatology, 175(4): 696-705, Feb. 27, 2016, 10 pages.
Third Party Submission filed in U.S. Appl. No. 17/109,311, filed Jun. 21, 2021, 21 pages.
Daniel Barolet et al., Radiant Near Infrared Light Emitting Diode Exposure as Skin Preparation to Enhance Photodynamic Therapy Inflammatory Type Acne Treatment Outcome, Lasers in Surgery and Medicine vol. 42, No. 2, Feb. 1, 2010, pp. 171-178.
Extended European Search Report, Application No. 18835929.3, dated Mar. 12, 2021, 10 pages.
Johanna T.H.M. Van Den Akker et al., Effect of Elevating the Skin Temperature During Topical ALA Application on in vitro ALA penetration Through Mouse Skin and in vivo PpIX production in Human Skin, Photochemical and Photobiological Sciences, Royal Society of Chemistry, Cambridge, GB, vol. 3, No. 3, Mar. 1, 2004, pp. 263-267.
Petras Juzenas et al., Uptake of Topically Applied 5-Aminolevulinic Acid and Production of Protoporphyrin IX in Normal Mouse Skin: Dependence on Skin Temperature, Photochemistry and photobiology, vol. 69, No. 4, Apr. 1, 1999, pp. 478-481.
International Search Report from PCT/US2018/042505, dated Oct. 2, 2018.
Letter to UVBiotek, LLC, dated Jul. 28, 2017, Re: K170187, Trade/Device Name: Photodynamic Therapy Device, available at https://www.accessdata.fda.gov/cdrh_docs/pdf17/K170187.pdf (accessed Apr. 30, 2020).
Webpage printout, Hill Laboratories Company, "Aklarus Phototherapy Treatment System with Red, Blue and Infrared Wavelengths by Hill Therapeutics," available at https://hilllabs.com/therapeutics/Aklarus-Photo-Therapy-System.php (accessed Apr. 30, 2020).
Maisch et al., Fluorescence Induction of Protoporphyrin IX by a New 5-Aminolevulinic Acid Nanoemulsion Used for Photodynamic Therapy in a Full-Thickness ex vivo Skin Model, Experimental Dermatology, 19, 2009, pp. e302-e305.
Nucci et al., Treatment of Anogenital Condylomata Acuminata with Topical Photodynamic Therapy: Report of 14 Cases and Review, International Journal of Infectious Diseases, 14S, 2010, pp. e280-e282.
USPTO Non-Final Office Action, U.S. Appl. No. 16/631,205, dated Mar. 3, 2022, 31 pages.
Willey et al., American Society for Laser Medicine and Surgery Abstracts, #147, Ultra Fast Thermal PDT for Facial Aks: Proof of Concept Study, Mar. 2017, 2 pages.
Japanese Office Action in JP Appl. No. 2020-503004 and English Translation, dated Aug. 2, 2022 (6 pages).
U.S. Appl. No. 17/854,066, filed Jun. 30, 2022, Willey, Andrea.
U.S. Appl. No. 17/876,224, filed Jul. 28, 2022, Lundahl, Scott et al.
U.S. Appl. No. 17/889,115, filed Aug. 16, 2022, Boyajian, Thomas et al.
U.S. Appl. No. 17/942,353, filed Sep. 12, 2022, Boyajian, Thomas et al.
Maisch et al., "Fluorescent Induction of Protoporphyrin IX by a New 5-Aminolevulinic Acid Nanoemulsion Used for Photodynamic Therapy in a Full-Thickness ex vivo Skin Model," Experimental Dermatology, 19, © 2009, pp. e302-e305, Jul. 2010.
Notice of Allowance on U.S. Appl. No. 17/487,698 dated Oct. 4, 2022, 6 pages.
USPTO Office Action on U.S. Appl. No. 17/876,224 dated Sep. 27, 2022, 20 pages.
Office Action in Japanese Application No. 2019-555822 dated Nov. 1, 2022 and English translation thereof, 11 pages.
Japanese Office Action and English translation, Application No. 2019-555822, dated Jan. 11, 2022, 13 pages.
Australian Examination Report, Application No. 2020267186, dated Feb. 3, 2022, 4 pages.
Australian Examination Report, Application No. 2021107564, dated Apr. 4, 2022, 4 pages.
Notice of Allowance, U.S. Appl. No. 17/487,698, dated Apr. 29, 2022, 11 pages.
Ang et al., "Photodynamic Therapy and Pain: A Systematic Review", Photodiagnosis and Photodynamic Therapy 19 (Jul. 2017) 308-344.
Champeau et al., "Photodynamic therapy for skin cancer: How to enhance drug penetration?", Journal of Photochemistry and Photobiology B: Biology, vol. 197, Jul. 2, 2019.
Kim et al., "In vivo skin absorption dynamics of topically applied pharmaceuticals monitored by fiberoptic diffuse reflectance spectroscopy" Spectrochimica Acta Part A 66, Mar. 2007, 768-772.
Nishimura et al., "Iontophoretic Photosensitization of the Skin Re-evaluated by Colorimetric Imaging in Senile Patients," Bioimages 19, Jan. 2011, 1-6.
Warren et al., "Pain Associated with Aminolevulinic Acid-Photodynamic Therapy of Skin Disease", J Am Acad Dermatol. Dec. 2009; 61(6): 1033-1043.
Ye et al. "Evaluation of Hydrogel Suppositories for Delivery of 5-Aminolevulinic Acid and Hematoporphyrin Monomethyl Ether to Rectal Tumors," Molecules, Oct. 2016, 21, 1347, 1-12.
Office Action in U.S. Appl. No. 17/506,849 dated Aug. 17, 2023 (17 pages).

\* cited by examiner

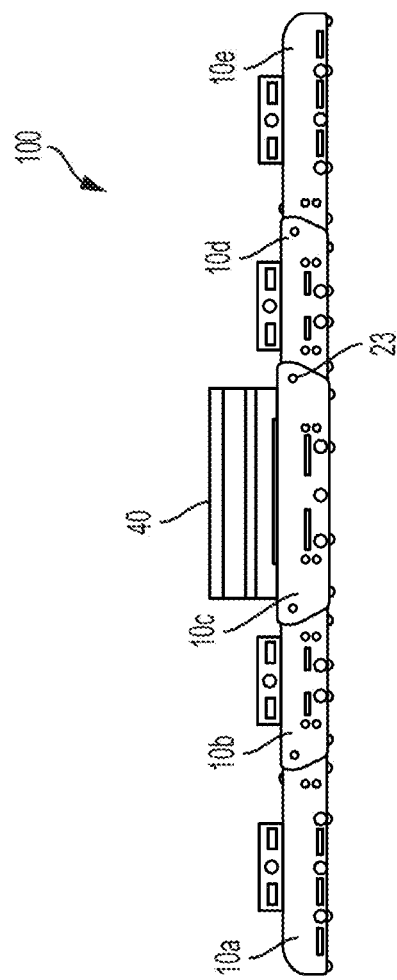
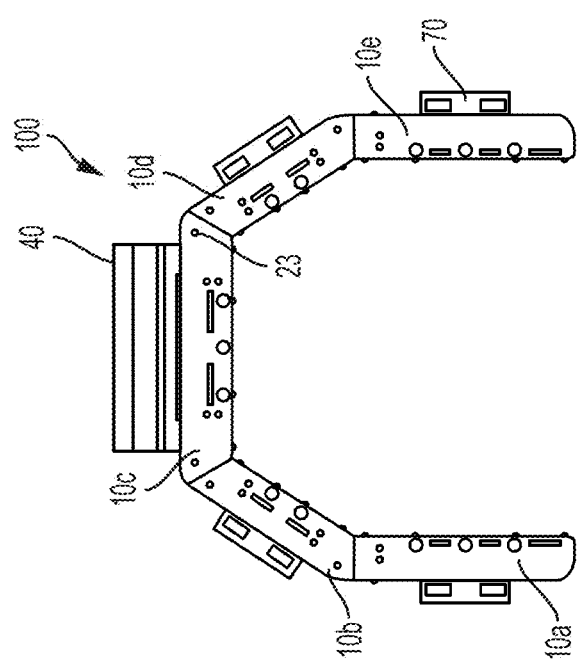

NODE OF CONTROL VOLUME
TEMP OF SKIN CONTACT THERMAL COUPLE
TEMP OF CONTROL REFERENCE THERMAL COUPLE]
SET TEMP 57C, HEAT ONLY
5 MIN SYSTEM WARM UP
4 MIN SKIN WARM UP
10 MIN HEAT IMMERSION

| NODE NUMBER | SKIN TEMP °C | CONTROL TEMP Ref. °C |
|---|---|---|
| 1 | 41.5 | 57.3 |
| 2 | 42.6 | 57.2 |
| 3 | 41.3 | 56.7 |
| 4 | 40.8 | 57.0 |
| 5 | 41.1 | 57.1 |
| 6 | 40.3 | 57.0 |
| 7 | 40.4 | 57.1 |
| 8 | 40.5 | 56.7 |
| 9 | 41.5 | 57.0 |
| 10 | 42.2 | 57.7 |
| 11 | 41.4 | 57.2 |

OUTSIDE OF CONTROL VOLUME

| NODE NUMBER | SKIN TEMP °C | CONTROL TEMP Ref. °C |
|---|---|---|
| 12 | 40.4 | 56.7 |

| NODE NUMBER | SKIN TEMP °C | CONTROL TEMP Ref. °C |
|---|---|---|
| \multicolumn{3}{c}{TEMP OF SKIN NO HEAT, LIGHT ONLY, 10mw/cm^2} |
| 10 | 31.2 | 24.2 |
| \multicolumn{3}{c}{TEMP OF SKIN NO HEAT, LIGHT ONLY, 20mw/cm^2} |
| 10 | 33.8 | 30 |
| \multicolumn{3}{c}{TEMP OF SKIN NO HEAT, LIGHT ONLY, 40mw/cm^2} |
| 10 | 37.7 | 30 |

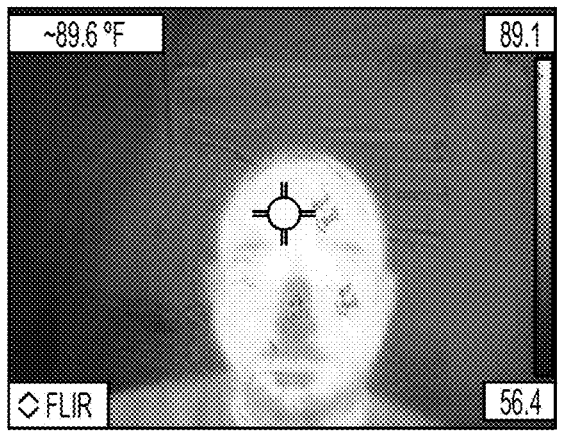
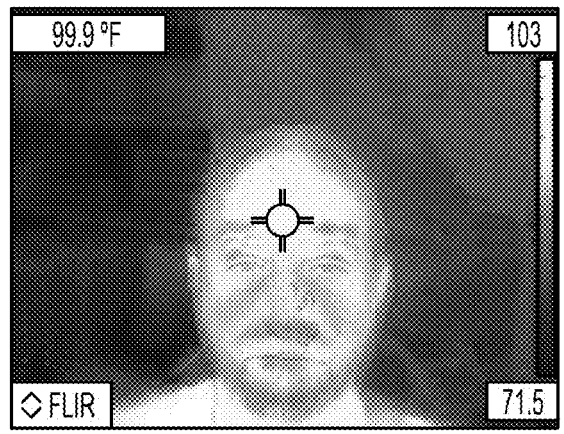
FIG. 14A    FIG. 14B
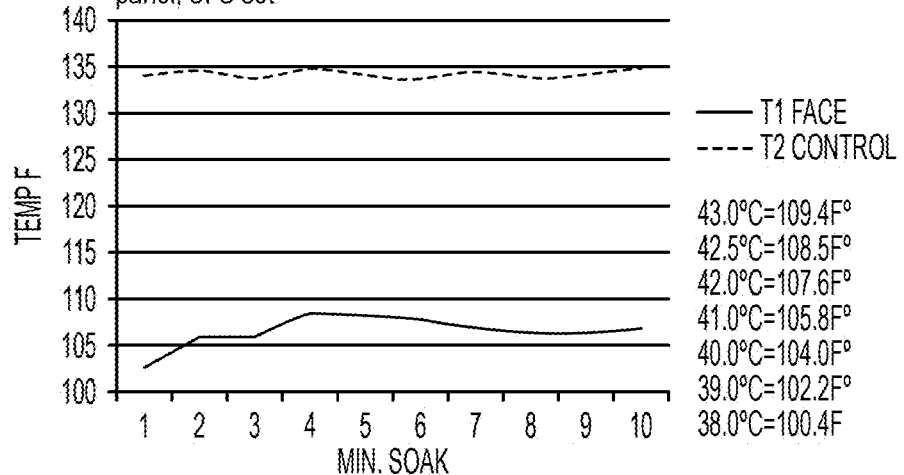
FIG. 14C
FIG. 14D

ADJUSTABLE ILLUMINATORS AND METHODS FOR PHOTODYNAMIC THERAPY AND DIAGNOSIS

CROSS-REFERENCE TO RELATED APPLICATION

This application is a divisional application of U.S. application Ser. No. 15/487,991, filed on Apr. 14, 2017, which is a continuation-in-part of U.S. patent application Ser. No. 15/292,731, filed on Oct. 13, 2016, and claims the benefit of priority to U.S. Provisional Application No. 62/241,902 filed on Oct. 15, 2015, the entire contents of all of which are hereby incorporated by reference in their entirety.

FIELD

The present disclosure relates generally to adjustable illuminators which provide a uniform distribution of visible light in a number of configurations and are suitable for use in photodynamic therapy and diagnosis, and to methods including operation of adjustable illuminators.

BACKGROUND

Photodynamic therapy (PDT), photodynamic diagnosis (PD), or photochemotherapy is generally used to treat and/or diagnose several types of ailments in or near the skin or other tissues, such as those in a body cavity. For example, PDT or PD may be used for treatment or diagnosis of actinic keratosis of the scalp or facial areas of a patient. In addition, PDT and PD may be used for treatment and diagnosis of other indications (e.g., acne, warts, psoriasis, photo-damaged skin, and cancer) and other areas of the patient (e.g., arms and legs).

During one form of PDT or PD, a patient is first administered a photoactivatable agent or a precursor of a photoactivatable agent that accumulates in the tissue to be treated or diagnosed. The agent or precursor may be administered to treat dermatological conditions, for example. The area in which the photoactivatable agent is administered is then exposed to visible light, which causes chemical and/or biological changes in the agent. These changes allow the agent to then selectively locate, destroy, or alter the target tissue while, at the same time, causing only mild and reversible damage to other tissues in the treatment area. One example of a precursor of a photoactivatable agent is 5-aminolevulinic acid ("ALA"), which is commonly used in PDT of actinic keratosis. As used here, the terms ALA or 5-aminolevulinic acid refer to ALA itself, precursors thereof and pharmaceutically acceptable salts of the same.

For effective treatment, it is desirable to have a power output that is uniform in intensity and color. Illuminators, such as those disclosed in U.S. Pat. Nos. 8,758,418; 8,216,289; 8,030,836; 7,723,910; 7,190,109; 6,709,446; and 6,223,071, which are incorporated by reference in their entireties for the techniques, methods, compositions, and devices related to PDT and PD, are typically used to provide the proper uniformity of light for treatment purposes. These devices generally include a light source (e.g., a fluorescent tube), coupling elements that direct, filter or otherwise conduct emitted light so that it arrives at its intended target in a usable form, and a control system that starts and stops the production of light when necessary.

SUMMARY

Because PDT can be used to treat a variety of treatment areas, some illuminators utilize two or more panels, each panel having a light source to emit light at the intended target area. These panels are coupled together so as to be rotatable relative to each other. By incorporating multiple, rotatable panels, the overall size and shape of the area that is illuminated can be changed according to the intended treatment area.

In conventional adjustable illuminators, the panels are equally sized by width and length and are typically driven at the same power level. The panels are further joined at their edges by hinges so as to be rotatable to achieve a desired configuration. However, due to the edges of the panels and the presence of the hinges, the light source(s) of one panel does not immediately adjoin the light source(s) of an adjacent panel. As a result, light is not emitted from a "gap" between the light sources. The lack of light emitting from such areas, together with the uniform supply of power to the panels, can cause optical "dead space" in certain portions of the target treatment area. These portions, in turn, receive less overall light, resulting in a lower dose of treatment in those portions. In some instances, the dose of treatment can be lowered by as much as a factor of five when compared with those areas receiving an optimal amount of light.

Generally, these conventional illuminators are used for phototherapy of acne, which typically does not require the administration of a photoactivatable agent for effective treatment. Thus, exposure to the light alone is generally sufficient treatment. Moreover, because multiple treatment sessions can be utilized to effectively treat the condition, uniformity of light across the target area during a given treatment is less of a concern in some situations. However, some forms of treatment involving PDT, such as the use of ALA to treat actinic keratosis, require specific and highly uniform intensity and color of light to achieve effectiveness. In these instances, successful PDT relies on the targeted delivery of both the correct quantity of the photoactivatable agent and the correct quantity (i.e., power and wavelength) of light to produce the desired photochemical reactions in the target cells. Thus, to achieve this, the light source must provide illumination to the target area and this illumination must be uniform with respect to both wavelength and power. The optical dead space that can occur at or near the hinges of conventional adjustable illuminators reduces the uniformity of the light along the treatment area, thereby reducing the effectiveness of PDT for these specific treatments. Moreover, these illuminators are also configured to adjust within a limited range, such that only a limited amount of surfaces on a patient's body may be treated, such as a patient's face and scalp. In addition, due to the various contours of a patient's body, the uniformity of light delivered by these conventional illuminators may vary substantially depending on the treatment area of the patient.

Therefore, it is an object of some embodiments of the present invention to reduce or eliminate these dead spaces and provide for a more uniform light distribution in an adjustable illuminator designed for PDT and/or PD of a variety of targeted areas. In addition, it is an object of some embodiments of the present disclosure to provide an infinitely adjustable illuminator that can effectively deliver a uniformity of light across various areas of a patient's body, such as a patient's extremities (e.g., arms and legs) or torso, in addition to a patient's face and scalp. Thus, a uniform light may be delivered to a targeted treatment area regardless of the shape and location of the contours of the patient's body.

One embodiment of the present disclosure includes a plurality of panels, wherein at least one panel is of a different width than the other panels. This panel is positioned between two other panels and, in a way, acts as a "lighted hinge" to provide enough "fill-in" light to reduce or eliminate the optical dead spaces when the panels are bent into a certain configuration. Preferably, five panels in total may provide for an optimal increase in the total size of possible treatment areas. Two of the panels are preferably of a smaller width than the other three larger panels. The panels are positioned in an alternating manner such that each of the smaller-width panels is situated in between two of the three larger panels to allow for both adjustability and increased uniformity. Furthermore, to further reduce or eliminate optical dead spaces, the panels are preferably coupled together by nested hinges, thereby reducing the area in which no light source is present on the illuminator. In order to even further reduce or eliminate optical dead spaces, it is preferable that the light sources on each of the panels are individually configurable to provide specific power output to certain areas of the light sources on the panels to compensate for decreased uniformity. For example, the power outputted to each individual diode in an array of light emitting diodes (LED) may be individually adjusted.

One embodiment of the present disclosure relates to an illuminator for photodynamically diagnosing or treating a surface, comprising a plurality of panels; a plurality of light sources, each mounted to one of the plurality of panels, the plurality of light sources configured to irradiate the surface with substantially uniform intensity visible light; and a heat source configured to emit heat to a patient between outer panels of the plurality of panels.

Another embodiment of the present disclosure relates to a method of photodynamically diagnosing or treating a patient, comprising controlling a heat source to direct heat to the skin of a patient during a first time period; and illuminating, during a second time period following the first time period, the patient with an illuminator having a plurality of panels to treat a dermatological condition, at least one of the panels being provided with at least one light source.

A further embodiment of the present disclosure relates to a method of photodynamically diagnosing or treating a patient, comprising illuminating the patient with an illuminator having a plurality of light sources, and during the illumination, emitting heat from a heat source so as to heat the skin of the patient, wherein illumination from the plurality of light sources commences at approximately the same time as emission of heat from the heat source toward the patient.

An additional embodiment of the present disclosure relates to a system comprising an illuminator for photodynamically diagnosing or treating a surface, comprising a plurality of panels; a plurality of light sources, each one mounted to one of the plurality of panels, the plurality of light sources configured to irradiate the surface with visible light; and at least one sensor configured to detect an orientation of at least one of the plurality of panels.

BRIEF DESCRIPTION OF THE DRAWINGS

Features, aspects, and advantages of the present disclosure will become apparent from the following description and the accompanying exemplary embodiments shown in the drawings, which are briefly described below.

FIGS. 1A-1B show top views of a main body of an illuminator according to an exemplary embodiment.

FIGS. 14A-D illustrate thermal data on a nodal basis, according to an embodiment.

DETAILED DESCRIPTION

Figure 2B:
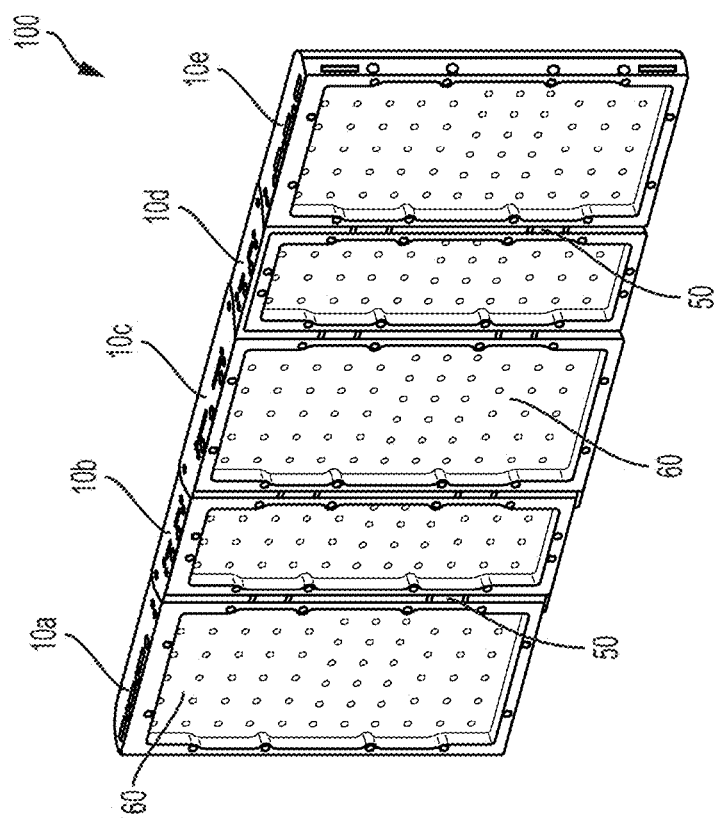
FIGS. 2A-2B show perspective views of the main body of the illuminator of FIGS. 1A-1B.

Various embodiments are described hereinafter. It should be noted that the specific embodiments are not intended as an exhaustive description or as a limitation to the broader aspects discussed herein. One aspect described in conjunction with a particular embodiment is not limited to that embodiment and can be practiced with any other embodiment(s).

As will be understood by one of skill in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member.

Unless otherwise indicated, all numbers expressing quantities of properties, parameters, conditions, and so forth, used in the specification and claims are to be understood as being modified in all instances by the term "about." Accordingly, unless indicated to the contrary, the numerical parameters set forth in the following specification and attached claims are approximations. Any numerical parameter should at least be construed in light of the number reported significant digits and by applying ordinary rounding techniques. The term "about" when used before a numerical designation, e.g., temperature, time, dosage, and amount, including range, indicates approximations which may vary by (+) or (−) 10%, 5% or 1%.

FIGS. 1A-1B and 2A-2B illustrate an embodiment of a configurable illuminator according to the present disclosure. The illuminator includes a main body 100, which preferably has five individual panels 10a-10e, each of which are connected in a rotatable manner via nested hinges 50. Each panel contains an array of light emitting diodes (LED) 60, which may be configured in an evenly spaced pattern across the face of the panel. The number of individual LEDs arranged in a given array is not particularly limited. Alternatively, other types of light sources may be used, such as fluorescent or halogen lamps.

Preferably, each LED array 60 extends as far to the edges as possible. In addition, the LED arrays 60 are preferably dimensioned to provide an overall lighted area for a given treatment area based on a range from the 5th percentile of corresponding sizes of female subjects to the 95th percentile of corresponding sizes of male subjects for that particular treatment area. The LED arrays 60 emit light at an appropriate wavelength according to the intended treatment or to activate the particular photoactivatable agent used in treatment or diagnosis. For example, when ALA is used as a precursor of a photoactivatable agent for the treatment of actinic keratosis, the LED arrays 60 preferably emit blue light having wavelengths at or above 400 nanometers (nm), for example, about 430 nm, about 420 nm or, for example, 417 nm. However, the LED arrays 60 may also emit visible light in other ranges of the spectrum, such as in the green and/or red ranges between 400 and 700 nm, for example, about 625 nm to 640 nm or, for example, 635 nm. For example, the LED arrays 60 may also emit light having wavelengths of 510 nm, 540 nm, 575 nm, 630 nm, or 635 nm. In addition, the LED arrays 60 may be configured to emit light continuously or the LED arrays 60 may be configured to flash the diodes on and off based on a predetermined interval. Furthermore, the LED arrays 60 may be configured such that only one wavelength of light (e.g., blue) is emitted. Alternatively, the LED arrays 60 may be configured such that two or more wavelengths of light are emitted from the arrays. For example, the LED arrays 60 may be configured to alternately emit blue light and red light for treatment purposes.

Figure 6:
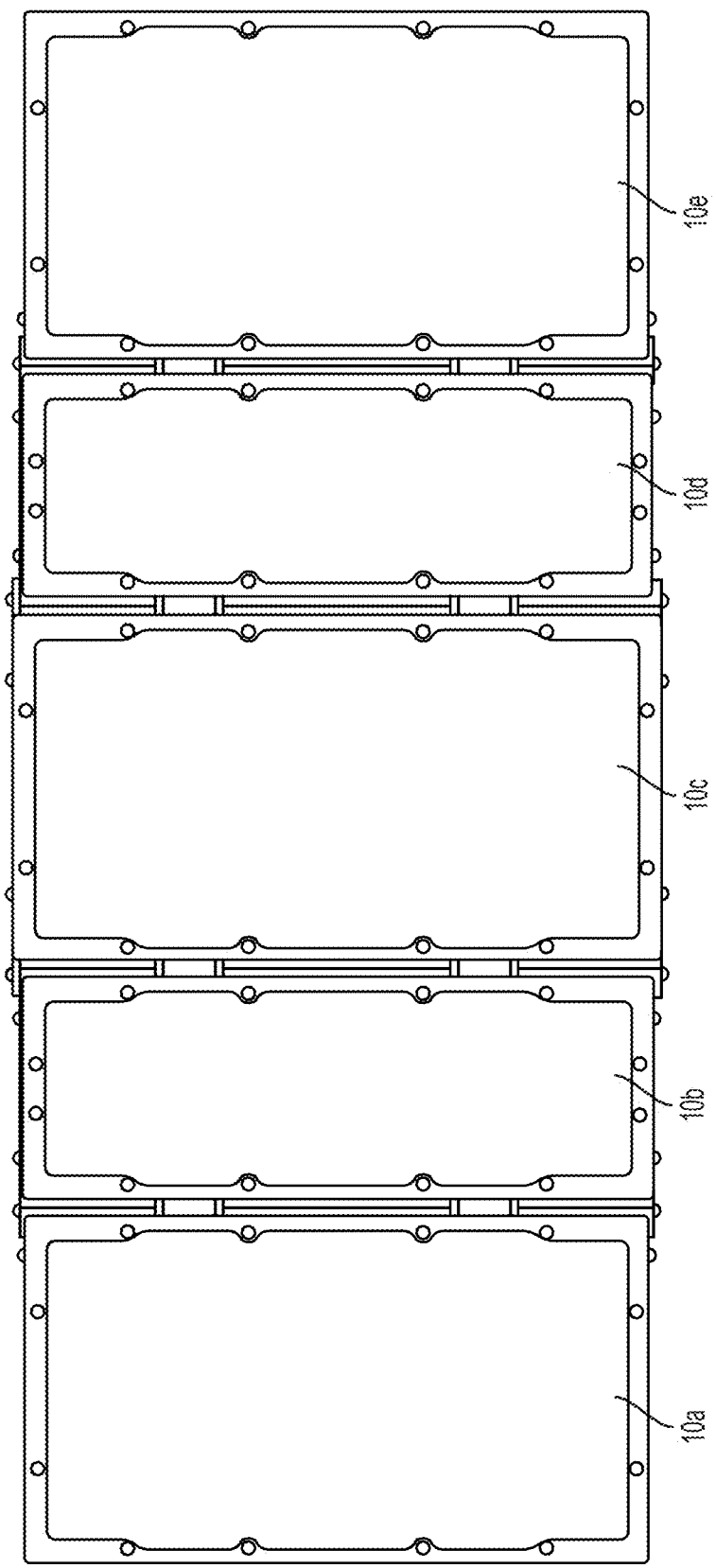
FIG. 6 shows a schematic view illustrating widths and lengths of individual panels of the main body of the illuminator of FIGS. 1A-1B.

As shown in FIGS. 1A-1B and 2A-2B, the five panels 10a-10e are of different widths relative to one another. In particular, in certain embodiments, three panels 10a, 10c, 10e are configured to have wider widths, while two panels 10b, 10d have smaller, narrower widths, each of the narrower widths of the two panels 10b, 10d being less than each of the wider widths of the three panels 10a, 10c, 10e. In some embodiments, the wider widths of the three larger panels 10a, 10c, 10e are approximately equal. In other embodiments, the wider widths of the three larger panels 10a, 10c, 10e are different relative to one another. In addition, the narrower widths of the two panels 10b, 10d may be approximately equal or may be different relative to one another. The panels are further arranged in an alternating configuration, with the narrower panels (e.g., 10b) positioned in between two wider panels (e.g., 10a, 10c). As shown in FIG. 6, in some embodiments, the narrower panels 10b, 10d are configured to have a width that is about 30% to 60% less than the width of the wider panels 10a, 10c, 10e.

In other embodiments, the narrower panels 10b, 10d are configured to have a width that is about 30% to 50% less than the width of the wider panels 10a, 10c, 10e.

Figure 2A:
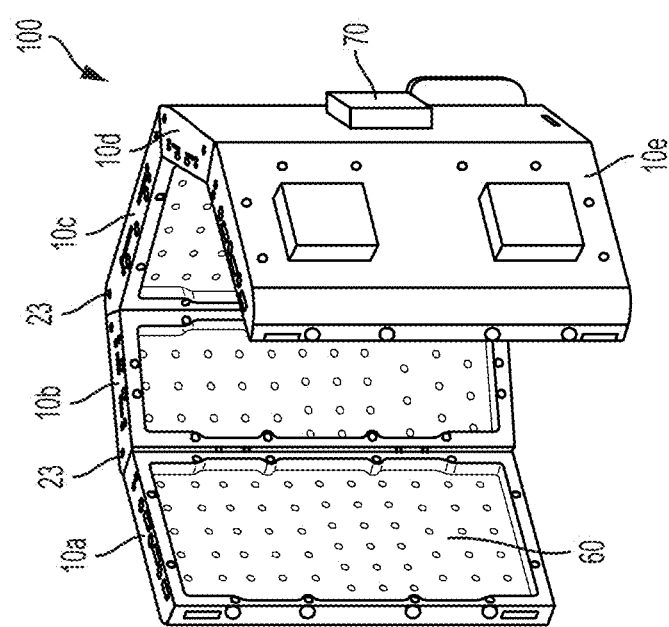

As shown in FIGS. 1A-1B and 2A-2B, the panels 10a-10e are rotatably connected by hinges 50. The hinges 50 may take the form of nested hinges, which may include hinges that substantially reduce or eliminate optical dead spaces. As shown in FIGS. 2A-2B, on at least one side of a panel, a tab 23 may extend out from both the top and bottom of the panel. The tabs 23 are configured such that a side of an adjacent panel may be received between the tabs 23, as shown in FIG. 2A. Thus, as seen in FIGS. 2A-2B and 6, the height of the adjacent panel (e.g., panel 10a) is slightly smaller than the height of the tabbed panel (e.g., panel 10b) into which the adjacent panel is received. As shown in FIG. 6, the middle panel (i.e., panel 10c) is preferably configured as having the largest height, such that it is tabbed on both sides and may receive the sides of adjacent panels on each side. As seen in FIGS. 1A-1B, each of the tabs 23 further includes an opening to receive a bolt to connect adjacent panels together.

The panels 10a-10e may be arranged such that side panels can move so as to expand a total footprint or coverage area of the panels 10a-10e, and may be configured to extend to portions of a patient such as the patient's chest or stomach. In at least one embodiment, at least one of the panels 10a-10e may be arranged such that at least one of the panels is provided in a flat or folded (bent or angled, for example) arrangement. The panels may be moved in a continuously variable manner. In at least one embodiment, one or more of the panels is provided with one or more detent mechanisms to retain the one or more panels in a desired position. The one or more detent mechanisms may be provided with the one or more panels such that the movement of the panels is restrained by the detent mechanisms to achieve a plurality of distinct panel configurations for treatment, in which the panels are kept in a specific position while a patient is being treated. The panels may be arranged relative to each other so as to achieve one or more particular configurations of the illuminator. In at least one embodiment, the panels may be arranged relative to each other such that the illuminator achieves at least one of a curved, flat or folded configuration, for example.

Figure 3A:
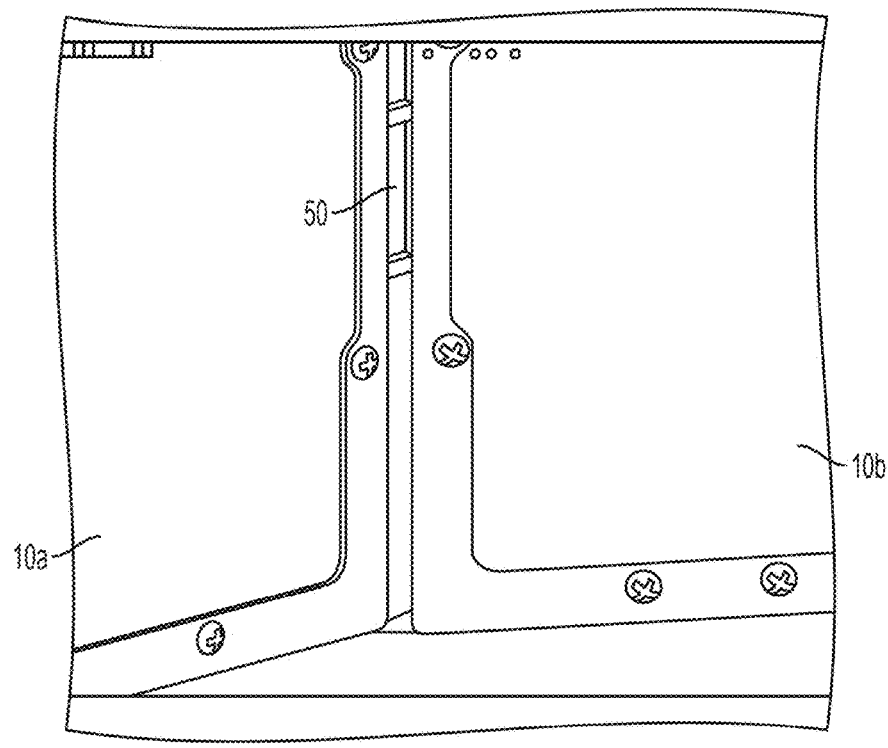
FIGS. 3A-3B show detailed views of the nested hinges of the main body of the illuminator of FIGS. 1A-1B.
Figure 3B:
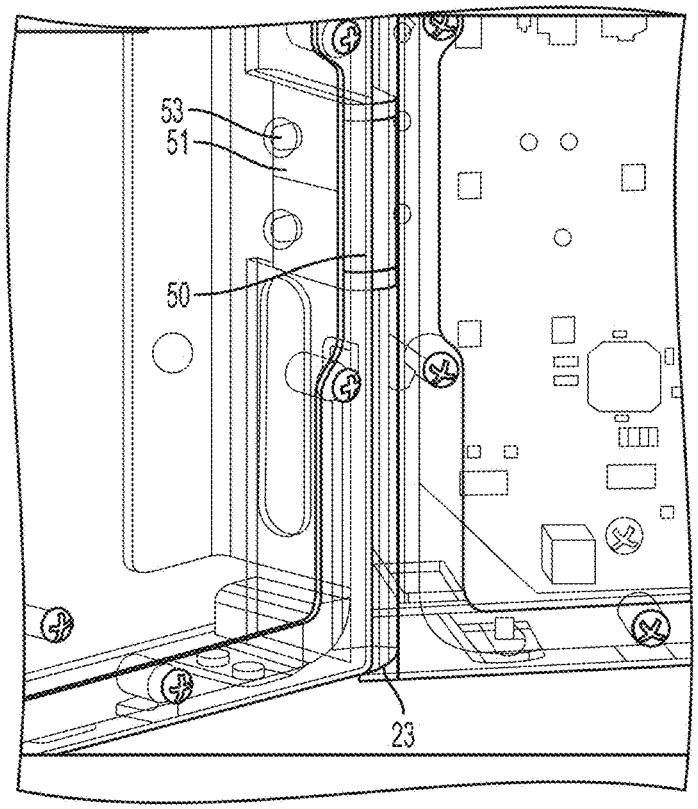

As shown in further detail in FIGS. 3A-3B, between the tabs 23 are the nested hinges 50, which are mounted to the inner side surfaces of adjacent panels (e.g., 10a, 10b) to allow for rotation of the panels. A flange 51 of the hinge 50 is mounted to the inner side surface of a panel via bolts 53. The inner side surface of a panel may include a recess in which the flange 51 may be placed. The inner side surface of the panel may also include an additional recess to accommodate the joint of the hinge 50 such that the joint of the hinge 50 becomes substantially flush with an outer front surface of the panel. Such configurations may allow for the outside vertical edges of adjoining panels to be positioned closer to one another. By spacing the vertical edges of adjoining panels closer, optical dead spaces may be further reduced or eliminated. In addition, the hinges 50 together with the tabs 23 may reduce the number of pinch points present in the system.

Figure 4:
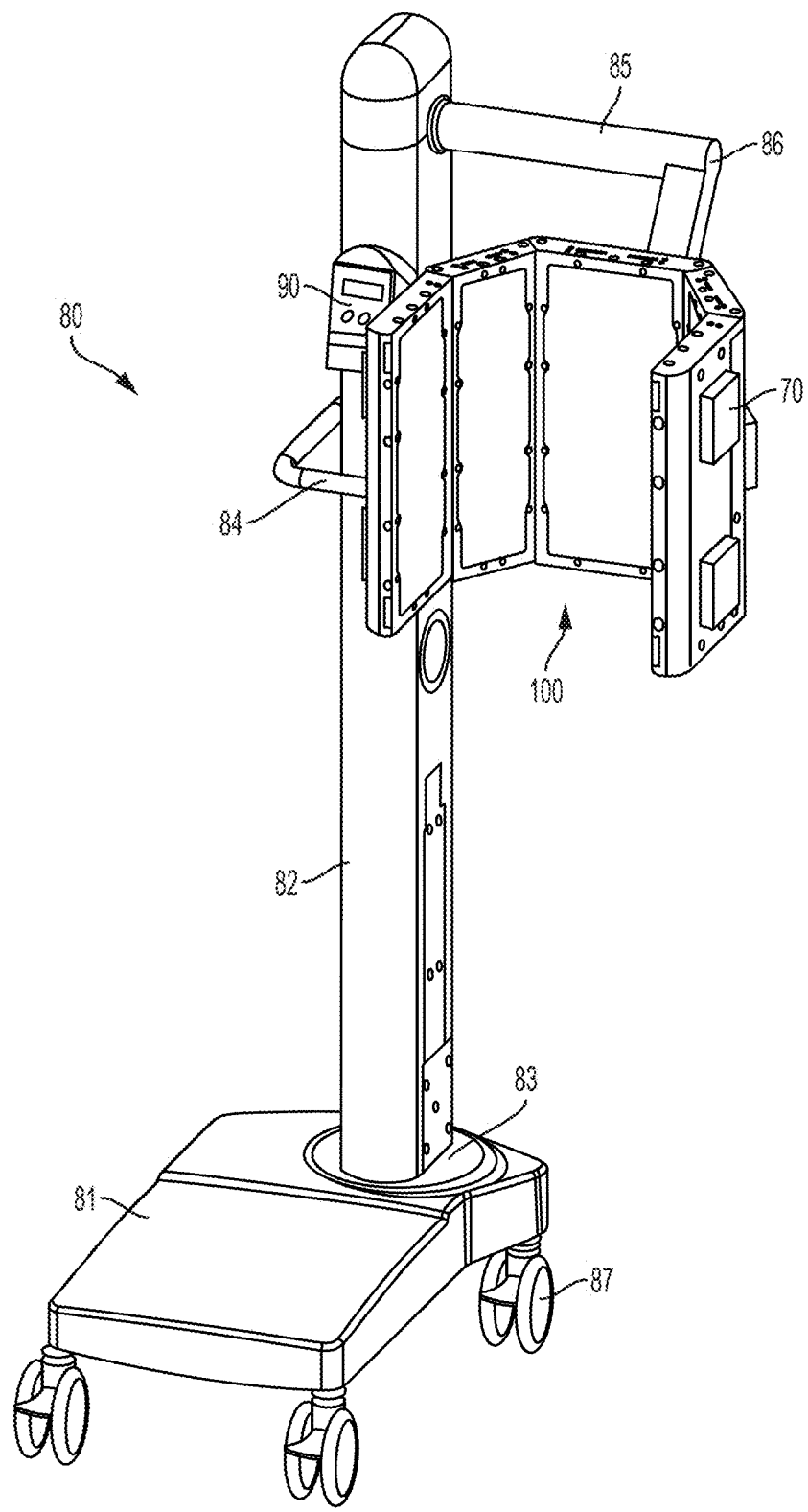
FIG. 4 shows a perspective view of the illuminator having the main body of FIGS. 1A-1B mounted to a stand.

As shown in FIGS. 1A-1B, the main body 100 of the illuminator may include a mounting head 40. The mounting head 40 may allow for the main body 100 to be mounted to a movable stand 80, which is shown in FIG. 4, to allow a user to easily move the main body 100 to the appropriate treatment position. The stand 80 includes a base 81 and a vertical pillar 82. The base 81 may further include wheels 87 at its bottom in order to allow the user to horizontally move the illuminator to an appropriate position. The wheels 87 may include locks, such that the stand 80 is prevented from further horizontal movement once positioned. In addition, the vertical pillar 82 may be attached to the base 81 at a pivot point 83. The pivot point 83 allows the vertical pillar 82 to be rotated to increase the range of positioning for the illuminator. At a top end, the vertical pillar 82 includes a connecting arm 85, which may serve as a mounting structure for the main body 100. The connecting arm 85 includes a hinge point 86 such that the main body 100 can be moved vertically relative to the stand 80. The vertical pillar 82 may also be configured as a telescopic structure, such that the user can change the height of the vertical pillar 82. This allows for an increased range of vertical movement for the main body 100, which can allow the user to position the main body 100 at lower portions of a treatment area, such as a patient's legs or feet. The stand 80 may also include a stabilization arm 84. Once the stand 80 and main body 100 is positioned, the stabilization arm 84 may be attached to the main body 100 to prevent unwanted movement of the main body 100 during treatment. As further shown in FIG. 4, a controller and power supply 90 is mounted to the stand 80 in order to supply electrical power to the main body 100 and allow the user to control the main body 100 for treatment purposes. Alternatively, the controller and power supply 90 may be directly mounted to the main body 100. In order to provide a cooling system for the LED arrays 60, one or more fans 70 may be mounted onto each of the panels, as shown in FIG. 4.

At least one controller (also referred to as a control unit) is also connected to the panels to regulate power to the lights to achieve the required uniformity and intensity for the target treatment. In at least one embodiment, the controller may also control output of a heat source 160 discussed in more detail below. In at least one embodiment, there may be a plurality of controllers controlling at least one dynamic process, e.g., controlling output(s) of one or more of: one or more light sources, one or more heat sources, and/or one or more air sources (such as a fan), in any combination. For example, separate controllers or integrated controllers may be provided for respectively controlling the output of LED arrays 60 and the heat source 160. In at least one embodiment, a first controller may control both light and heat sources, and a second controller may control an air source, for example.

The controller may be implemented as hardware, software, or a combination of both, such as a memory device storing a computer program and a processor to execute the program. Alternatively, each panel may have a dedicated controller to regulate power to the individual LED array on a given panel to allow for more particular calibration of the illuminator, which may further enhance uniformity and increase efficiency. For example, under Lambert's cosine law, light intensity at a given point on a "Lambertian" surface (such as skin) is directly proportional to the cosine of the angle between the incoming ray of light and the normal to the surface. Thus, a ray of light that is directed to the front of a curved surface (e.g., a head of a patient) will arrive in a substantially perpendicular manner to that area and will result in 100% absorbance. However, a ray of light that arrives at a side edge of the curved surface will arrive in a substantially parallel manner. According to Lambert's cosine law, the intensity, and thus absorption, of the light at the side edge will approach zero, making treatment at that area ineffective. Thus, a "fall off" of light exposure tends to occur at the edges of a curved surface. In addition, "fall off" increases as the distance between the light source and the point on the surface increases.

Configuring an illuminator to conform to the curved surface (e.g., a U-shaped configuration designed to "wrap around" the curvature of the surface) aids in reducing this effect and increases overall uniformity. However, to sufficiently increase uniformity, the light source should be larger relative to the target treatment area in order to fully encompass the body part to be treated and also provide light from all angles to any target point on the treatment area. In order to increase the uniformity of light exposure to the treatment area while maintaining a practical size of the illuminator, the LED arrays 60 may be individually configured to increase the intensity of light emitting from certain diodes to compensate for this fall-off effect.

Figure 5:
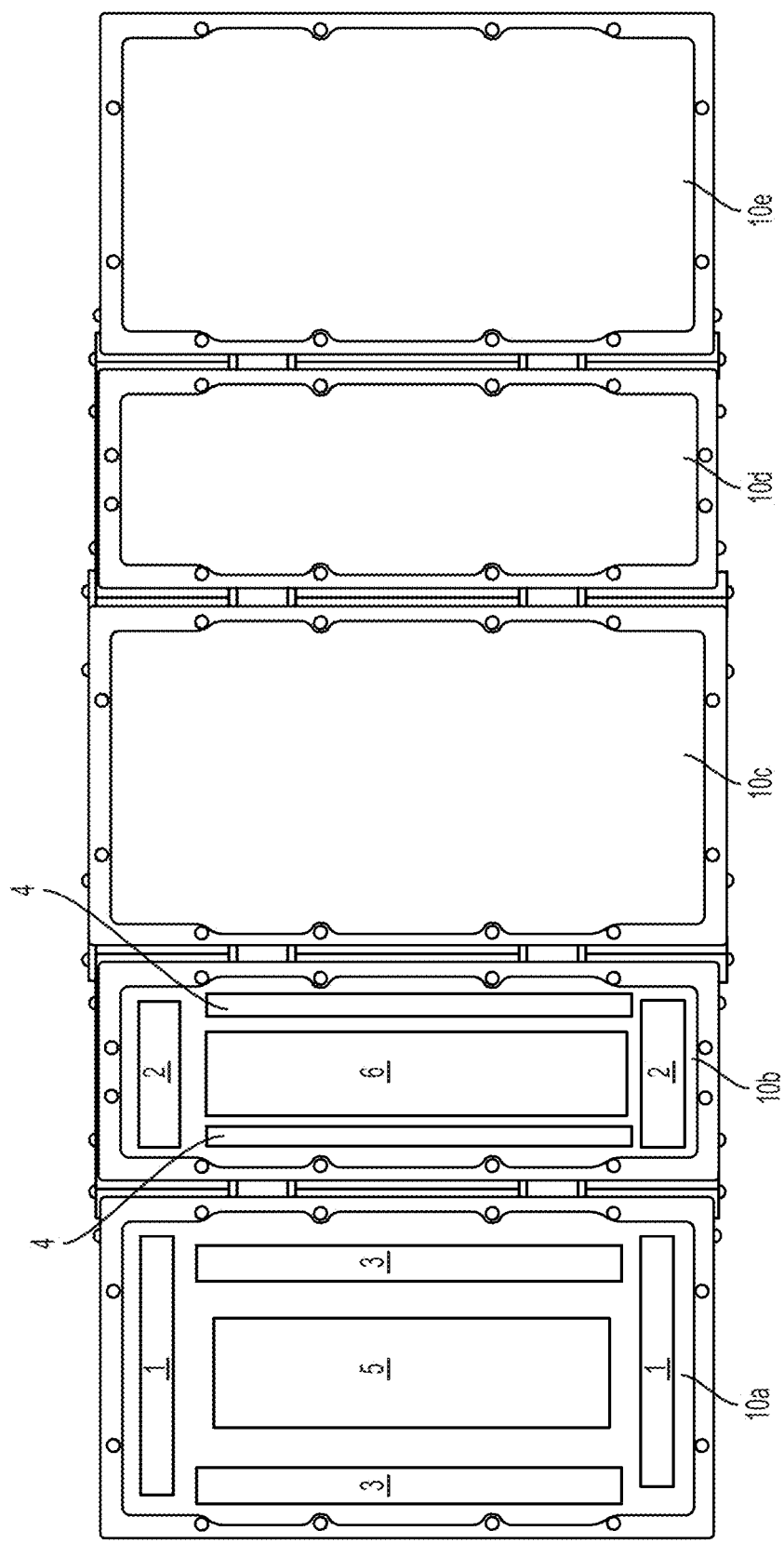
FIG. 5 shows a schematic view illustrating an addressable configuration of LEDs mounted on the main body of the illuminator of FIGS. 1A-1B.

An example in which the LED arrays 60 may be individually configured is shown in FIG. 5. Here, the LED arrays 60 are divided into three general areas, which may be described as "addressable strings." Areas 1, 3, and 5 correspond to an addressable string configuration that may be included in the wider panels 10*a*, 10*c*, and 10*e*, while areas 2, 4, and 6 correspond to an addressable string configuration that may be included in the narrower panels 10*b* and 10*d*. The current to each area is adjusted in order to adjust the intensity of light emitting from each of the areas. For example, a higher current may be supplied to areas 1 and 2 than the current supplied to areas 3 and 4 such that areas 1 and 2 emit a higher intensity of light than areas 3 and 4. Similarly, a higher current may be supplied to areas 3 and 4 than the current supplied to areas 5 and 6. Thus, a higher intensity of light is emitted overall from the edges, which may allow for a reduction in any fall-off effect. Alternatively, the illuminator may be configured to adjust each individual diode present in a given LED array 60, allowing for an even greater calibration effect (that is, fine tuning).

Furthermore, by using either pre-programmed settings or sensors to detect the curvature of the surface to be treated, the LED arrays 60 can be individually configured to emit more intense light to only those areas that require it. Additionally, pre-programmed sensors can be used to detect the orientation of one or more panels (e.g., whether a panel is curved or folded flat) and may be used to configure the LED arrays 60 to emit more or less intense light in areas that require it. In particular, in at least one embodiment, at least one sensor detects an orientation of at least one panel and provides detection information (a detection result) to the controller. The sensors may include one or more encoders, such as one or more angle encoders, which are provided at one or more locations on the panels. In at least one embodiment, at least one sensor is a microswitch configured to sense a position of at least one panel. In some embodiments, a plurality of sensors may include an encoder, a microswitch, or combinations thereof. The sensors are communicated with the controller and are configured to provide information about the panel orientation, such as an angle at which a panel is disposed, to the controller. The controller then controls the intensity of light in accordance with a detection result. In at least one embodiment, a plurality of sensors provides information to the controller so that the controller may carry out a determination as to whether the illuminator has a configuration that is one of a plurality of preset configurations. For example, the controller may store, in a memory, information relating to one or more preset configurations (e.g., for a bent illuminator, a flat illuminator, etc.).

When the controller receives information transmitted from the sensors, the controller may compare the sensed information to the preset configurations to determine a match between the sensed information and one or more preset configurations. The controller may further store a protocol for altering intensity which is executed upon determining a match between the sensed information and the preset configuration. For example, if the illuminator is detected to be a curved illuminator, the controller implements a light intensity output which is correlated to the preset protocol for a curved illuminator. The controller may further compare an existing intensity to an intensity associated with a particular configuration and determine whether the intensity should be adjusted. This allows for an increase in uniformity of light exposure in an efficient manner as power output and/or light intensity is increased to only certain diodes, in accordance with need. In at least one embodiment, a plurality of preset configurations may be presented to a clinician or practitioner, e.g., on a touch screen, who may then select the preset configuration corresponding to the physical arrangement of the illuminator in the clinical environment.

The addressable strings of the LED arrays 60 may also include varying amounts of individual diodes mounted within the particular area. For example, for the wider panels 10a, 10c, and 10e, 12 diodes may be mounted in each of areas 1, while 9 diodes may be mounted in each of areas 3, and 41 diodes may be mounted in area 5, resulting in a total of 83 individual diodes included within each of the wider panels 10a, 10c, and 10e. For the narrower panels 10b and 10d, 8 diodes may be mounted in each of areas 2, while 9 diodes may be mounted in each of areas 4, and 23 diodes may be mounted in area 6, resulting in a total of 57 individual diodes included within each of the narrower panels 10b and 10d. However, the number and arrangement of diodes included within each of the LED arrays 60 is not particularly limited. For example, the wider panels 10a, 10c, and 10e may each contain a total amount of diodes that ranges from about 80 diodes to about 350 diodes. Similarly, the narrower panels 10b and 10d may each contain a total amount of diodes that ranges from about 50 diodes to about 250 diodes. By varying the arrangement of the diodes within each of the addressable strings of the LED arrays 60, power output and/or the intensity of light emitted from a given array may be better controlled and fine-tuned.

In addition, individually regulating power to the LED arrays 60 can also contribute to the reduction or elimination of the optical dead spaces that may otherwise occur at the hinge points. Specifically, power output and/or the emitted light intensity may be increased close to the edges of the array that are closest to the nested hinges to compensate for the lack of light emitting from the meeting point of panels. The narrower panels 10b, 10d are also preferably operated at a higher power level and/or at a higher emitted light intensity compared to the wider panels 10a, 10c, 10e in order to provide additional fill-in light. Furthermore, individual power regulation may aid in compensating for manufacturing variance that can occur in individual diodes. Finally, by fine-tuning each array 60, the panels can be easily deployed for other applications as each array is specifically configurable to address the lighting needs of the specific application.

The illuminator may further include a timer, which can indicate to the user the appropriate length of exposure time for the particular treatment. The illuminator may also be programmed with pre-stored light dosing parameters to allow the user to select a desired treatment type. The pre-stored parameters may include, for example, pre-stored settings for exposure time, light intensity, and outputted wavelength. Based on the selected treatment, the illuminator is automatically configured to provide the correct lighting dosage by being supplied with the appropriate power output to achieve the required uniformity for the treatment. Alternatively, the illuminator can be provided with sensors that detect the size of the treatment area positioned in front of the illuminator. The sensors then determine the correct light dosing parameters based on the sensed treatment area. The illuminator may also further include actuators and may be programmed to be moved automatically depending on the selected treatment. Once a treatment is selected, the illuminator may be automatically positioned into the proper configuration by the actuators without requiring the user to move the system by hand. Alternatively, the sensors may detect the adjusted position of the illuminator manually set by the user. The detected position of the illuminator may then be used to indicate the intended treatment area. Correct light dosing parameters for the specific treatment area may then be provided based on the detected position set by the user.

The illuminator of the present disclosure allows for an infinite amount of configurations that can be adapted for the targeted treatment area. The configurations may range from a flat-plane emitter (as shown in FIGS. 1B and 2B) to a substantially U-shaped configuration (as shown in FIGS. 1A and 2A). The adjustable illuminator may also be configured such that the two end panels 10a, 10e can be pulled back relative to the three middle panels 10b, 10c, 10d, such that a smaller U-shaped configuration may be created by the middle panels. Thus, the adjustable illuminator allows for the treatment of additional areas of a patient's body. In other words, not only can the adjustable illuminator effectively deliver a uniform light intensity to traditional surfaces such as the face or scalp, but the adjustable illuminator can also provide a device that can easily be configured to treat other portions of a patient's body, in particular, those having smaller curved surfaces, such as the arms and legs. Moreover, the adjustable illuminator may also be easily positioned to deliver a uniform light intensity to larger treatment areas, such as the back or chest.

Figure 7:
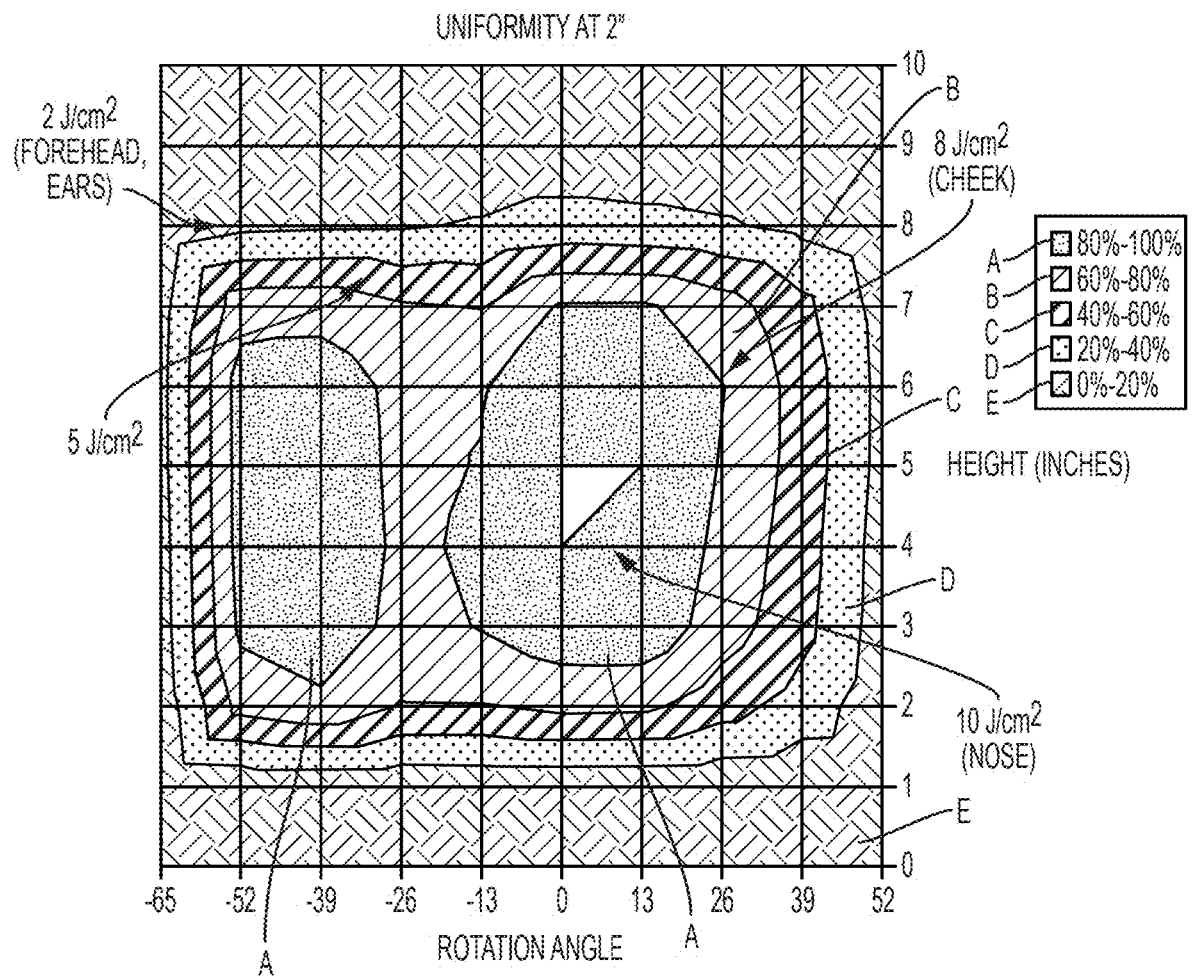
FIG. 7 shows a graph illustrating light dosage across a treatment area according to a conventional paneled illuminator.

As described above, the narrower panels 10b, 10d are dimensioned such that the panels act as "lighted hinges." Thus, when the wider panels 10a, 10c, 10e are adjusted into the desired form, the illuminator "bends" at the narrower panels 10b, 10d, where traditionally the "bend" would occur substantially at the hinge itself. Thus, instead of an unlighted "bent" portion as would occur in the conventional illuminator, the present illuminator provides a "bent" portion that is also configured to emit light, thereby helping to reduce optical dead space without requiring large amounts of power differentiation among the light sources of each panel to provide the required fill-in light. The effects of this configuration can be best seen in a comparison of FIGS. 7 and 8. FIG. 7 illustrates the light uniformity produced by a conventional illuminator, measured with a cosine response detector, which mimics the response of a patient's skin to the incident of light as described above, at a distance of two inches. Total light dose, in terms of $J/cm^2$, was measured based on emitted irradiance ($W/cm^2$) over time (in seconds). The targeted treatment area shown is a patient's head, where height is shown as the y-axis and rotation angle from the center of the emitting surface is shown as the x-axis. As can be seen in FIG. 7, higher light doses of about 10 $J/cm^2$ occur at the center of the face (for example, at region A), near the patient's nose, where the patient is facing closest to, and substantially perpendicular to, the middle-most panel. Total light dose then begins to drop as movement away from the center of the face occurs where the effects of cosine "fall-off" and optical dead spaces are more prevalent. For example, light dose is reduced by about 20% at the patient's cheek areas (for example, at region B), and by about 80% toward the outer boundaries of the patient's face (for example, at region E), such as the ears and forehead. Thus, as shown in FIG. 7, conventional adjustable illuminators utilizing equally-sized panels operating at the same power output level produce a varying field of light uniformity, making it undesirable and ineffective for those treatments requiring highly specific light uniformity.

While certain embodiments described above relate to an illuminator comprising a plurality of panels, other embodiments may include an arcuate illuminator without individual rectilinear panels. For example, in at least one embodiment, the illuminator may be constructed of at least one curvilinear member. Further, the arcuate illuminator may have substantially curved portions extending from a substantially flat portion provided between the substantially curved portion. The patient's face may be positioned so as to be opposed to the substantially flat portion, such that at least three sides of the patient's head are surrounded by the illuminator. For example, the patient's face may be directly opposed to a first portion of the illuminator, while the left and right sides of the patient's head may be opposed to second and third portions, respectively.

Figure 8:
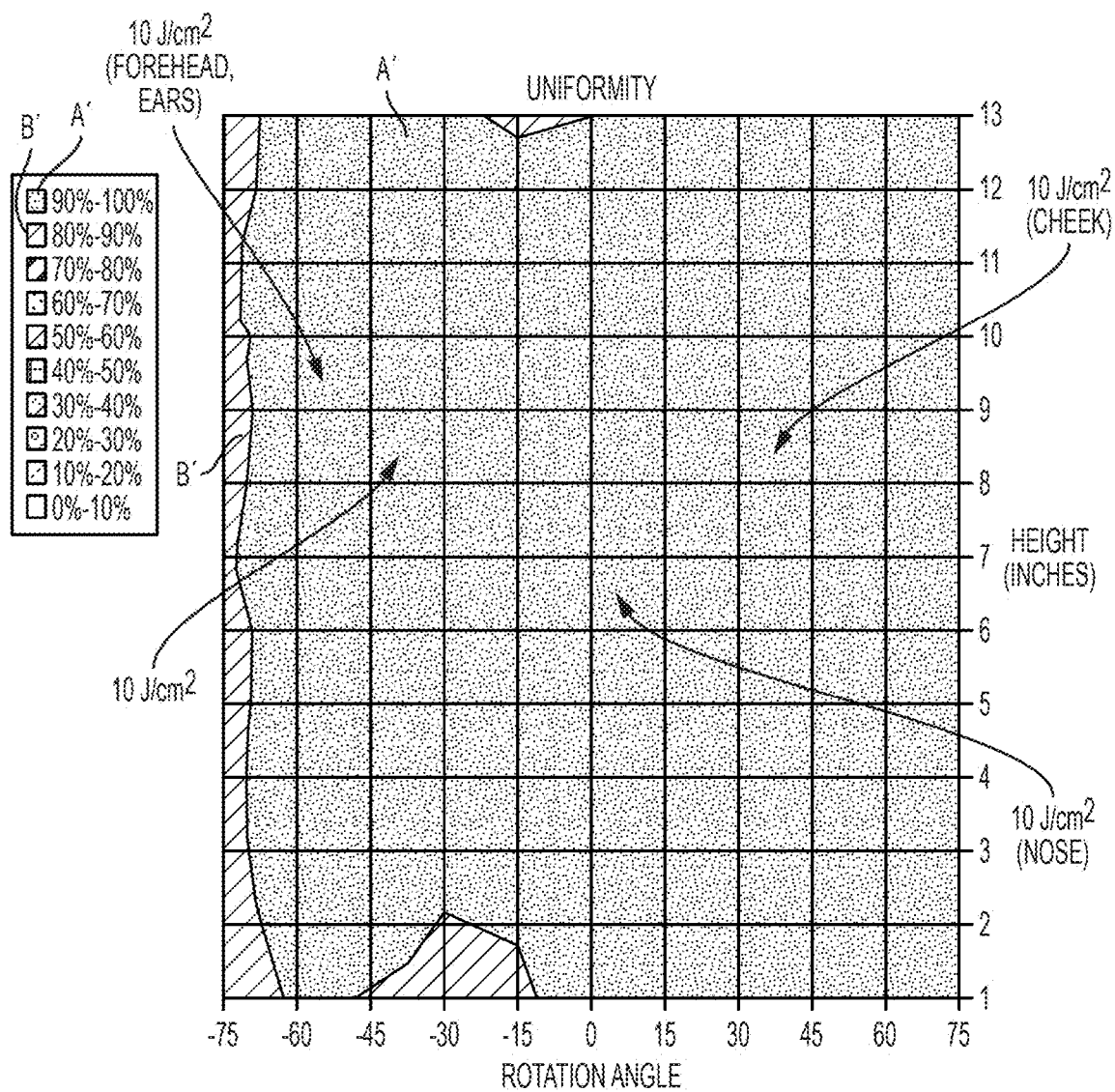
FIG. 8 illustrates a graph illustrating light dosage across the same treatment area as FIG. 7 using an illuminator according to an embodiment.

FIG. 8, on the other hand, illustrates the light uniformity produced by an embodiment of the present disclosure. The targeted treatment area is the same as that measured in FIG. 7. However, compared to FIG. 7, the light output uniformity produced by the illuminator is greatly enhanced across the patient's face and exhibits little to no deviation from the light output measured in the center of the patient's face to the light output measured at the edges of the patient's face. For example, as shown in FIG. 8, total light doses of about 10 $J/cm^2$ (for example, at region A') are provided across all regions of the face, including the center of the face (for example, the patient's nose), the patient's check areas, and the outer boundaries of the patient's cheek areas, such as the ears and forehead. Moreover, total light dose drops off minimally (for example, at region B') at the extreme outer boundaries of the patient's face. In one embodiment, the measured output over an active emitting area (over the entire active emitting area) is within 60% of the measured maximum (over the entire active emitting area) measured with a cosine response detector over all operation distances. More preferably, the measured output over the emitting area is within 70% of the measured maximum over a distance of two and four inches. Even more preferably, the measured output over the emitting area is within 80% of the measured maximum over a distance of two and four inches.

One example of a treatment method for precancerous lesions, such as actinic keratosis, by PDT utilizing an adjustable illuminator described above in conjunction with ALA will now be described.

Essentially anhydrous ALA is admixed with a liquid diluent just prior to its use. The ALA admixture is topically applied to the lesions using a point applicator to control dispersion of the ALA admixture. The admixture may be applied in accordance with the techniques disclosed in U.S. patent application Ser. No. 15/371,363, filed on Dec. 7, 2016, which is hereby incorporated by reference in its entirety for the background, apparatuses and methods described therein. After the initial application of the ALA admixture has dried, one or more subsequent applications may be similarly applied. Approximately 10-20% solution of ALA is administered. Formation of photosensitive porphyrin and photosensitization of the treated lesions occurs over the next ½-18 hours, during which time exposure to direct sunlight or other bright light sources should be minimized. Between ½ and 18 hours after administration of the ALA, the lesions are irradiated by the adjustable illuminator according to the present disclosure. The illuminator irradiates the lesions with a uniform blue light for a prescribed period. According to a preferred treatment, the visible light has a nominal wavelength of 417 nm.

Such embodiments thus provide a method for photodynamically diagnosing or treating a contoured surface of a patient, which includes providing the adjustable illuminator described above, placing the patient in the illuminator, and illuminating the patient to diagnose or treat the patient. The patient may be illuminated to treat actinic keratosis, acne, photo-damaged skin, cancer, warts, psoriasis, or other dermatological conditions. The method may also be used to remove hair and diagnose and treat cancer.

Since the total light dose ($J/cm^2$) is equal to irradiance ($W/cm^2$) multiplied by time (sec), one parameter that needs to be controlled for delivery of the correct treatment light dose is exposure time. This may be accomplished by the timer described above, which can control the electrical power supplied to the LED arrays 60 appropriately, and which can be set by the physician. Data has shown that 10 $J/cm^2$ delivered from a source with an irradiance density of 10 $mW/cm^2$, or an irradiance density of about 9.3 to about 10.7 $mW/cm^2$, produces clinically acceptable results for desired treatment areas (e.g., face, scalp, extremities). From the equation above, this light dose will require an exposure time of 1000 seconds (16 min., 40 sec). In addition, due to the addressable nature of the adjustable illuminator, the illuminator may be used to treat a patient at higher power such that less time is required for effective treatment. For example, the adjustable illuminator may deliver an irradiance density of 20 $mW/cm^2$ for an exposure time of 500 seconds (8 min. 20 sec) to deliver a clinically acceptable light dose of 10 $J/cm^2$. Alternatively, the adjustable illuminator may include higher power ranges, such as 30 $mW/cm^2$, over an exposure time resulting in a light dose of 10 $J/cm^2$. A selected light dose may also be administered by additionally or alternatively varying the irradiance density over treatment time. In at least one embodiment, a parameter which is controlled is the temperature to which the illuminator is heated, as discussed below.

According to one embodiment, a method of treatment includes warming up an illuminator so as to cause heat to be emitted from the illuminator, and exposing a patient's skin to the illuminator. The heat accelerates the conversion of the ALA to porphyrin (e.g., photosensitive porphyrin or proto porphyrin). The relationship between temperature exposure and ALA conversion is non-linear, and the enzymatic pathways responsible for the conversion are highly sensitive to temperature. In at least one embodiment, increasing the temperature by approximately 2° C. may approximately double the rate of production of protoporphyrin IX (PpIX), for example. In at least one embodiment, increasing the heat output of the illuminator, e.g. by approximately 2° C., may produce an effect after about 20 minutes of treatment which is comparable to that realized over the course of 1-3 hours of treatment, without increased temperature.

In particular, a method according to one embodiment includes turning on a light such as LEDs 60, and turning on a heating element of the illuminator. The method may include turning on both the LEDS 60 and the heating element simultaneously, such that light and heat are both applied during a treatment period. The method may further include turning on the LEDs 60 after a period in which the heater heats up (e.g., a 5 minute warm-up period). For a treatment period of about 20 minutes, the total acceptable light dose delivered to the patient may be approximately 10-20 J/cm². The treatment period in an exemplary embodiment may be from about 10 minutes to about 1 hour. The total acceptable light dose in an exemplary embodiment may be about 10-40 J/cm². In at least one embodiment, the treatment period may be longer than 1 hour or shorter than ten minutes, and the acceptable light dose may be less than 10 J/cm² or more than 40 J/cm², depending on the clinical circumstances.

In at least one embodiment, the LEDS 60 and a heating element (a heat source) 160 may not be turned on simultaneously, but in a consecutive manner. For example, first, the ALA may be applied. Next, the heating element may be activated, to apply heat to the patient's skin for a first treatment period for a thermal soak, which may be 20-30 minutes, for example. It has been found that the surface temperature of a face will stabilize in about 5 minutes. Following the first treatment period, light may be applied for a second treatment period, e.g., about 8-15 minutes. The total light dose delivered to the patient may be approximately 10-20 J/cm². In some embodiments, at least a portion of the heat may be delivered through one or more heating pads positioned on a patient's skin. In at least one embodiment, such a process is carried out for treating a dermatological condition of the patient, for example. The treatment period in an exemplary embodiment may be from about 10 minutes to about 1 hour. The total acceptable light dose in an exemplary embodiment may be about 10-40 J/cm². In at least one embodiment, the treatment period may be longer than 1 hour or shorter than ten minutes, while the acceptable light dose may be less than 10 J/cm² or more than 40 J/cm², depending on the clinical circumstances.

Additionally, in at least one embodiment, a method of treatment further includes recording data indicative of temperature for at least one node in a volume, and recording data indicative of temperature for at least one additional node in the volume. The volume may be a control volume of cubic or other form corresponding at least in part to a portion of the patient's skin which is exposed to the illuminator.

Figure 9A:
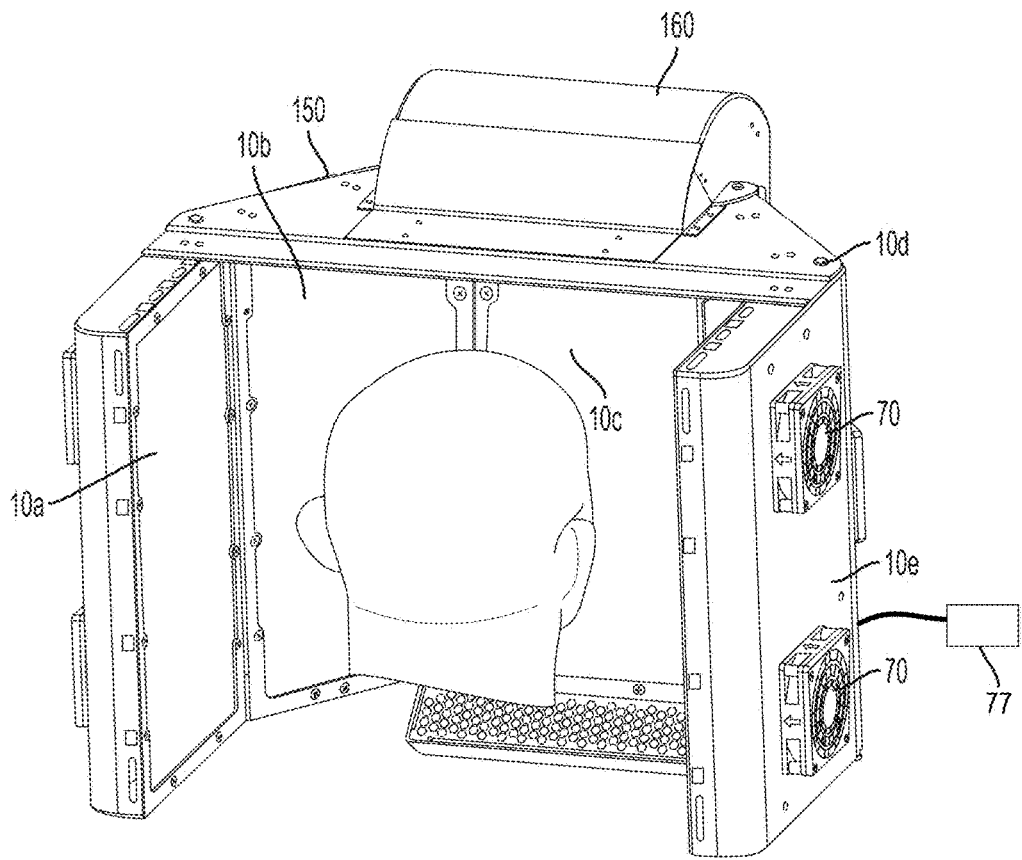
FIGS. 9A and 9B illustrate an illuminator according to an embodiment.
Figure 9B:
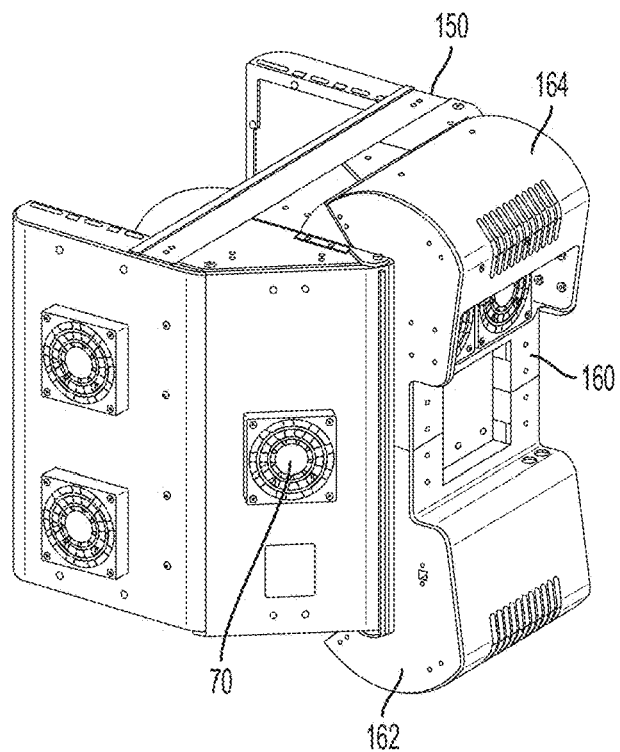

FIGS. 9A and 9B illustrate an apparatus according to an embodiment of the present disclosure. The apparatus is an illuminator including certain components shown, for example, in FIGS. 2A-2B. The illuminator includes a frame 150 into which panels 10a-10e are assembled. In addition to the panels 10a-10e, a heat source (heating element) 160 is assembled in the frame 150. For example, as shown in FIG. 9B, the heat source 160 may be sandwiched between panels 10b, 10d and positioned at least partially behind panel 10c. The heat source 160 may include curved terminal portions 162, 164 which project beyond the panels, such that at least a portion of the heat source is not obstructed by the panels and is directly exposed to the patient. In at least one embodiment, the heat source 160 may be an infrared quartz heater. Together the panels 10a-10e, frame 150, and portions 162, 164 create a partially enclosed space which retains a bath of warm air into which a portion of the patient (e.g., the patient's head) may be immersed.

In at least one embodiment, the heat source 160 may comprise frame mounted resistance tape heaters. In at least one embodiment, the heat source 160 may comprise a plurality of heaters, including at least one selected from the group including IR LEDs, resistance cartridge heaters, positive temperature coefficient heaters, or IR quartz heaters, as mentioned above. In at least one embodiment, the IR quartz heater is relatively responsive and produces a sufficient heat output, and may be readily controlled, e.g., by a controller 77, which may be a proportional integral derivative (PID) controller. Further, the IR quartz heater is relatively compact and may be integrated into the frame 150 without requiring enlargement of the frame 150.

The heat source 160 may be equipped with at least one controller (a control unit), such as the controller 77 to heat output to the target treatment. The control unit may be a controller implemented as hardware, software, or a combination of both, such as a memory device storing a computer program and a processor to execute the program. In at least one embodiment, the heat source 160 is controlled by a PID controller with monitoring and over/under temperature limit control. In some embodiments, the controller may further include one or more of an input/output (I/O) expansion module and a data logging and field communications access module. The controller may be a microprocessor regulator with software framework drivers programmed to control an input set temperature to a specified tolerance based on feedback from a reference control thermistor 170 discussed below. In at least one embodiment, the heat source is configured to output sufficient heat to reach a predetermined skin or tissue temperature target, e.g., 40° C.±2° C.

Figure 9C:
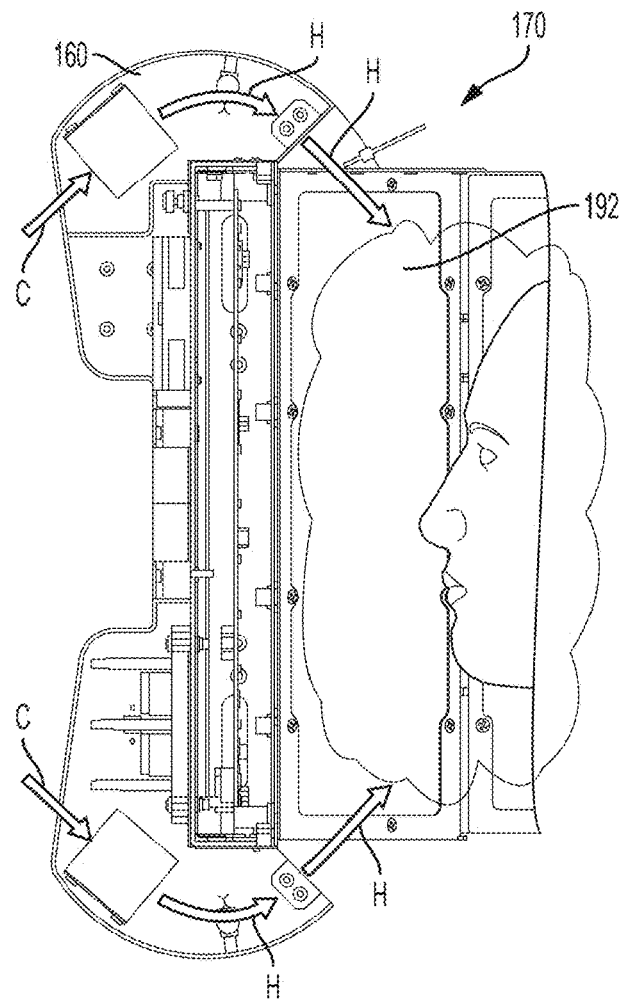
FIG. 9C illustrates an illuminator according to an embodiment.

FIG. 9C illustrates an illuminator according to an embodiment. In at least one embodiment, the illuminator further includes one or more thermistors. The thermistors may be integrated into the illuminator or provided in a kit including a suite of diagnostic tools. In at least one embodiment, a negative temperature coefficient or a positive temperature coefficient thermistor may be provided as a reference control thermistor 170 disposed on or near the heat source 160. In at least one embodiment, the thermistor 170 may be arranged at a portion of the heat source 160 proximate to an upper portion of panel 10c. A temperature measured by the reference control thermistor 170 may be compared to a temperature measured at the exposed skin of the patient, e.g., by a temperature probe placed on the patient's forehead, such as a contact thermocouple. In some embodiments, one or more thermocouples may be used to ascertain a relationship between the skin temperature (thermocouple temperature) and a temperature sensed by thermistor 170 (a control temperature or thermistor temperature).

In particular, the one or more thermocouples may be used to ascertain a relationship between skin temperature and control temperatures when the illuminator is originally manufactured, or when a first diagnosis is carried out. For example, a reference or control temperature may be set based on experimentally derived data, and a reference or control temperature against which the thermocouple temperature is compared may be temperature value from a table stored in a memory of a control unit connected to the illuminator. In at least one embodiment, the thermistor may be a programmable thermistor in which one or more temperature values are stored, and after the thermistor is programmed, it may be used to regulate the heat output of heat source 160. The comparison of temperatures may be carried out at one or more locations across the exposed skin of the patient. For example, by carrying out temperature measurement at a plurality of locations across the patient's face, a thermal map of the patient's face may be constructed. A thermal mapping may be performed before and after treatment. Further, the results of the thermal mapping may be compared, e.g., to a user's needs as articulated in a treatment or clinical plan. The results of a patient's thermal mapping may be compared to one or more other patient's thermal mapping data.

In at least one embodiment, the heat source 160 may be used in conjunction with fans 70. For example, the fans 70 may be operated to circulate cooling air through the system. Further, cool air or room temperature air, which travels along a path indicated by arrows labeled 'C' in FIG. 9C, may be directed toward a heat exchanger in the heat source 160. The heat exchanger heats the cool air. The heated air, which travels along a path indicated by arrows labeled 'H' in FIG. 9C, may be blown at relatively gentle flow rates. In at least one embodiment, the fans 70 are controlled by a controller to provide an air speed of approximately 3-6 knots and a volumetric flow rate of 14 cubic feet per minute (CFM). In some embodiments, the fan speed may be constant or variable. In at least one embodiment, a controller (which may be a controller that controls at least one of the LEDs 60 or heat source 160) controls the fans 70. The controller may control the output of one or more of fans 70 by varying the revolutions per minute (RPM) of fans 70, for example. The heated air may be blown by fans 70 toward the face of the patient, e.g., from a top and bottom of the heat source 160. The air flow creates a bath or pocket of heated air which substantially arounds the patient's skin, such that the patient's face, for example, may be enveloped in warm air. The thermodynamic behavior of the system may allow for controlling the disparity between the temperature at the patient's skin (measured with the contact thermocouple) and the temperature measured by the thermistor, so as to be within about 15° C., for example. In at least one embodiment, the surface of the patient's skin (e.g., their facial skin) attains a stable temperature within five minutes of when the heat from the heat source 160 is emitted.

Control of the thermodynamic transfer behavior allows for the air that is being blown and the heat output by the heat source to be modulated in accordance with a desired heating effect of the skin. In at least one embodiment, a desired raise in skin temperature (e.g., by 2° C.) may be achieved by determining a rise in air temperature and a corresponding time period. That is, the controller may be programmed to determine how high and for how long the temperature should be raised in order to heat a patient's skin to a desired level. Further, in at least one embodiment, the controller may also make such a determination with respect to air speed and/or volumetric flow rate. Such determinations by the controller may be made with reference to one or more maps stored in the memory of the controller. For example, one such map is a map correlating the temperature of thermistor 170 to a rise in skin temperature. Another such map is a map correlating the thermistor temperature to the air speed and the volumetric flow rate of the air. The air speed and volumetric flow rate themselves vary at least in part based on the configuration of heat source 160, and more particularly, how the curved portions (plenums) 162, 164 are structured and arranged. In at least one embodiment, the one or more maps stored in memory may correlate one or more of the thermistor temperature, a desired skin temperature, a volumetric flow rate, an air speed, and an air temperature to each other. The controller may reference information from one or more such maps to carry out a precise control of skin temperature. The system may be provided with a plurality of sensors for sensing temperature at a plurality of locations, and the controller may reference the aforementioned maps containing data from such sensors to control the heat source 160 at one or more locations. Further, by taking into account information from the thermal heat maps, heating of the skin at multiple points may be controlled in accordance with a treatment plan. In one embodiment, the use of such map allows the desired skin temperature to be obtained without directly measuring the skin temperature by one or more temperature sensors on the skin, for example.

Figure 9D:
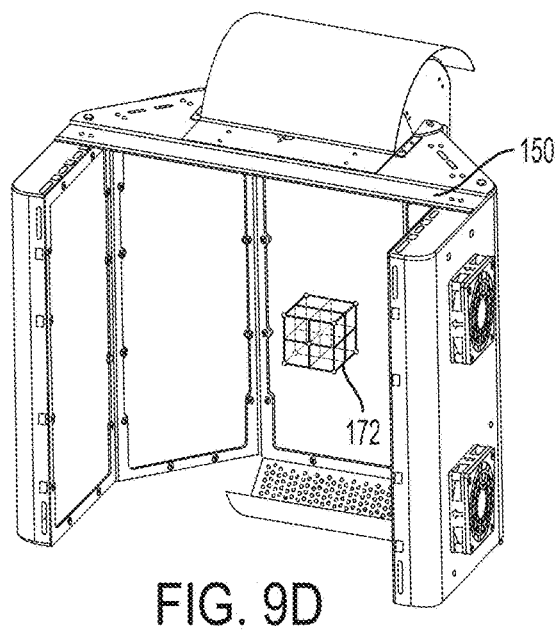
FIG. 9D illustrates an illuminator according to an embodiment, in which heat is emitted to a control volume, e.g., a cubic volume.
Figure 9E:
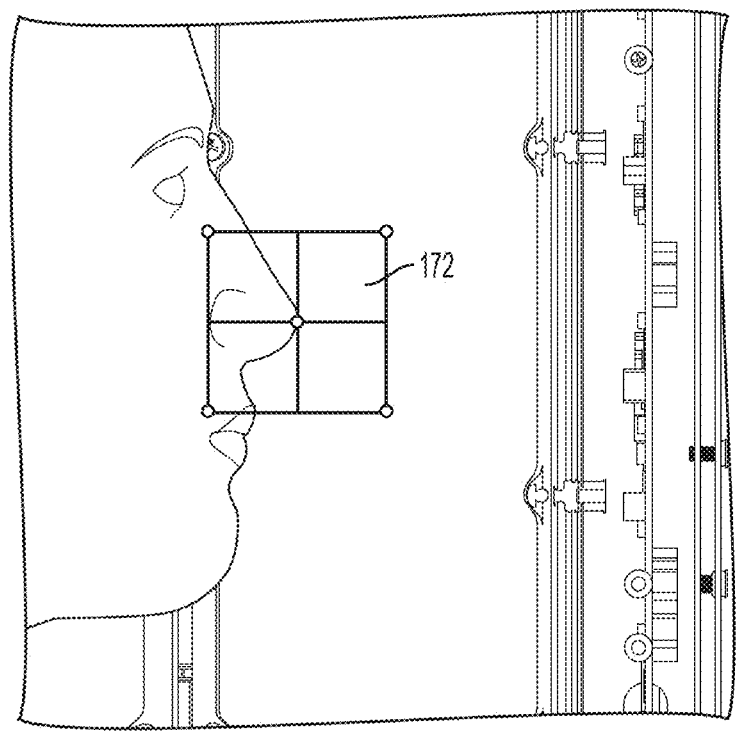
FIG. 9E depicts a control volume according to an embodiment.
Figure 9F:
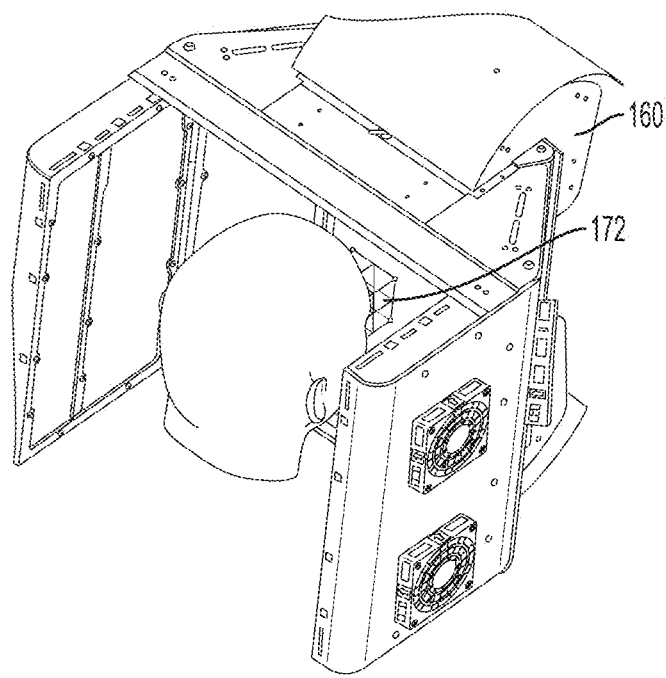
FIG. 9F is a perspective view showing a configuration according to an embodiment.

FIG. 9D illustrates an illuminator according to an embodiment, in which heat is emitted to a control volume, e.g., a cubic volume. In at least one embodiment, the heat source 160 may emit heat to a treatment target, such as a target within a cubic volume 172 as shown in FIG. 9D. The cubic volume 172 may have a total height of 6", and the temperature may be measured at a plurality of points in the x, y and z directions of the cubic volume 172. For example, the temperature may be sensed at 3" from a center panel 10c, where a predetermined treatment target is disposed at a center of the cubic volume 172. FIG. 9E depicts the cubic volume 172 wherein a treatment target is a patient's nose, centered in the volume. FIG. 9F is a perspective view showing an exemplary positioning of a patient with respect to the heat source 160 and illuminator.

Figure 10:
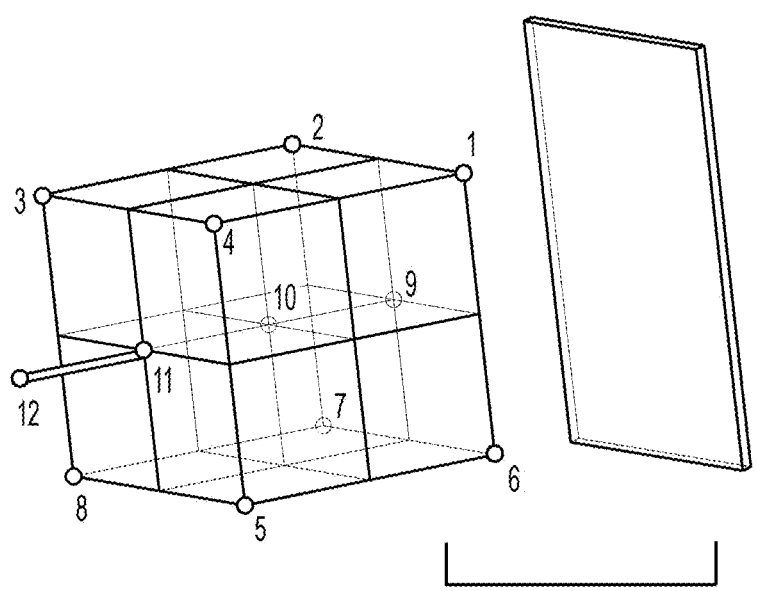
FIG. 10 illustrates a cubic volume at which a plurality of nodes are defined.

FIG. 10 illustrates a volume with respect to which nodes 1-12 may be defined, with node 10 being a centermost node within the volume, and node 12 being a node outside the volume (e.g., at a distance from the volume). The temperature may be measured at any or all of the nodes so as to construct a thermal map. In at least one embodiment, the data may be recorded every minute, or at a different predetermined time interval. In at least one embodiment, the cubic volume 172 is established as a measurement framework. Measurements of temperature (and measurements of distance from one or more of panels 10) may be taken at one or more of the nodes and compared, for example, to the temperature taken at the thermistor 170. In this manner, the positioning of the patient may be controlled with respect to the illuminator to ensure that the total acceptable light dose is achieved.

Figure 11A:
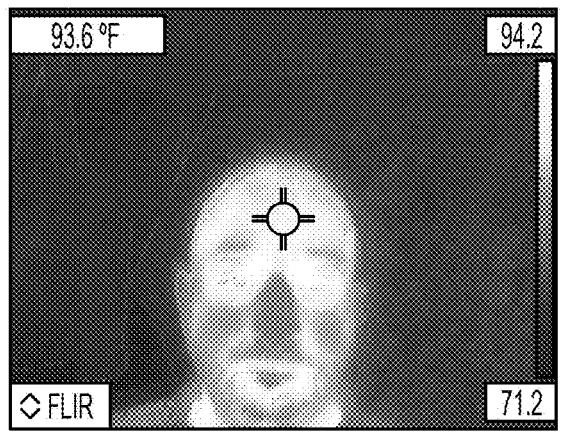
FIGS. 11A-B illustrate thermal data according to an embodiment.
Figure 11B:
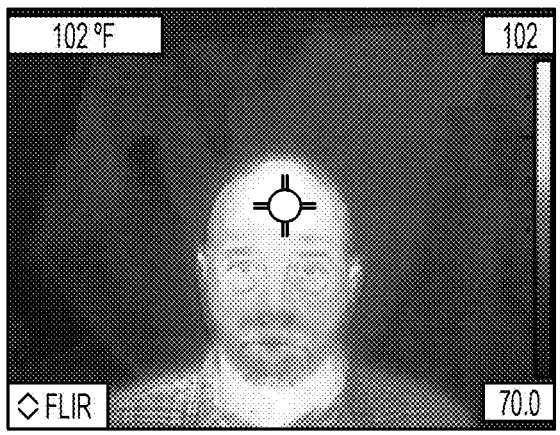

FIGS. 11A-B illustrate thermal maps according to an embodiment. FIG. 11A depicts a thermal map of a patient's skin, prior to application of heat. Prior to application of heat, the average skin temperature was 93.6° F. In at least one embodiment, the heat source 160 may be warmed up for five minutes, and the patient may then be exposed to light from light source 60 and heat from heat source 160 for about 10 minutes. FIG. 11B depicts a thermal map after a five-minute warm up period of the heat source 160 and a ten minute thermal soak. After the warm-up period and ten minute heat soak, the average skin temperature was 102° F. In at least one embodiment, selected forced convection may be used, as it may have fewer instabilities and narrower variation in temperature over a heated target. Further, in at least one embodiment, an indirect heat application may be employed, such that the patient's skin does not directly contact the heat source 160. Rather, heat is emitted at a distance from the patient's skin, and the controller determines a proposed emission pattern based on the results of a comparison between a plurality of temperature measurements taken at nodes of the control volume 172 to a temperature measurement taken by thermistor 170.

In at least one embodiment, the controller may turn the heat source 160 on or off through firmware that takes feedback from the temperature of thermistor 170 and has a firmware setting of +/−1 degree. In at least one further embodiment, a non-contact infrared (IR) sensor, such as a laser infrared sensor, may be used to detect skin temperature and supply the sensed skin temperature data to the controller. The input from the non-contact IR sensor may be provided in one or more maps stored in the controller, as further data indicative of skin temperature. In at least one embodiment, during an initial warm-up period (e.g., five minutes), when the heat source 160 is beginning to warm up, the system is not yet at a steady state where it can be controlled to deliver a desired output, but is in a transient state. The non-contact IR sensor may allow for the patient's skin temperature to be detected and for the detection result to be compared to skin temperature values for a plurality of patients. Such skin temperature data may be data derived from a sample population and stored in a map in the controller. If a given patient's skin temperature is colder than an average skin temperature, the controller may accelerate heating up of the heat source 160 in order to promote warming up of the patient's skin in a more efficient manner. Alternatively, if the patient's skin temperature is comparable to or warmer than the average skin temperature, the warm-up process may not be accelerated, but may continue normally.

In at least one embodiment, a high skin or tissue temperature was between about 40.3-42.6° C., with an average skin temperature of 41.3° C. Thermal testing was conducted with application of only light or heat, or both light and heat, at 10 mW/cm$^2$ and 20 mW/cm$^2$. Thermal testing indicated that light itself did not appear to influence the temperature of skin on the patient's face, when the heat was on.

Figures 12A, 12B, 12C:
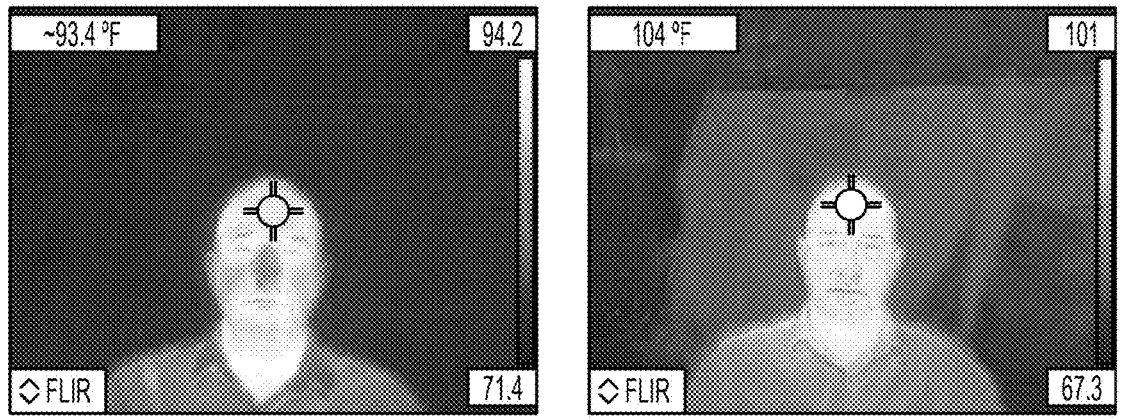
FIGS. 12A-D illustrate thermal data without application of light.
Figure 12D:
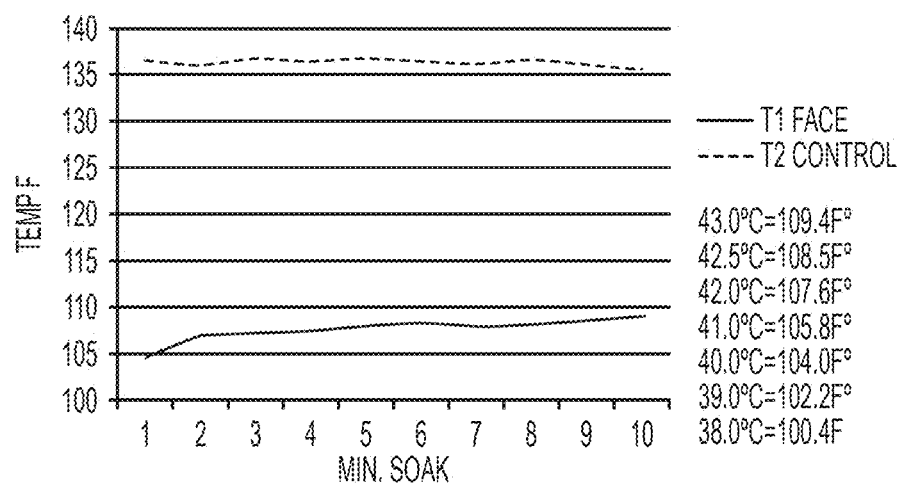

FIGS. 12A-D illustrate thermal data without application of light. More particularly, FIG. 12A depicts a thermal map of a patient's skin or tissue temperature before heat was applied, while FIG. 12B depicts a thermal map after heat was applied in a 10 minute soak. FIG. 12C shows skin temperature (thermocouple temperature) and thermistor temperature data for nodes 1-12. FIG. 12D depicts a plot of the thermocouple and thermistor temperature over time, during the thermal soak, for the center node 10.

Figures 13A, 13B:
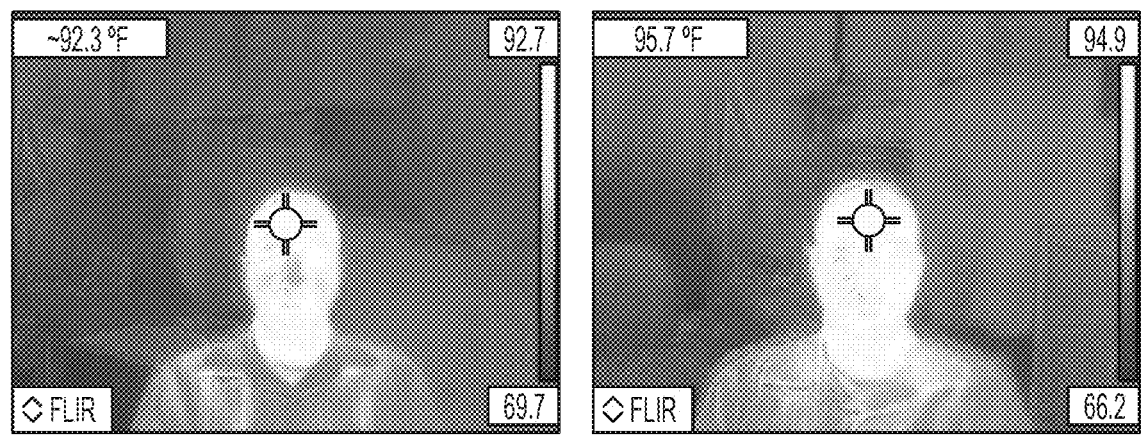
FIGS. 13A-D illustrate thermal data without application of heat.
Figures 13C, 13D:
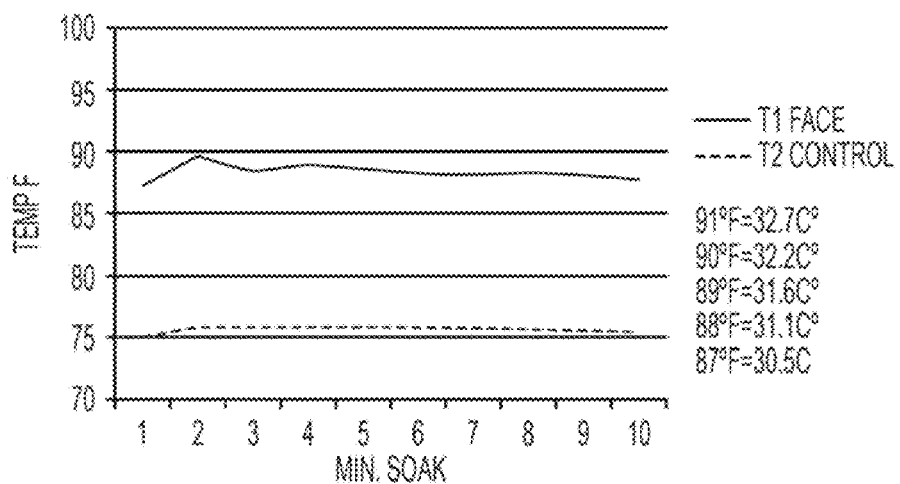

FIGS. 13A-D illustrate thermal data without application of heat. In particular, FIG. 13A depicts a thermal map of a patient's skin or tissue, without applying heat. FIG. 13B depicts a thermal map following light treatment. FIG. 13C shows temperature data (thermocouple and thermistor data) for the center node 10. FIG. 13D depicts a plot of the thermocouple and thermistor data over time, in a treatment protocol where the heat source 160 was not turned on. In particular, FIG. 13D reflects a "light-only" treatment, where there may be an elapse of a predetermined time period between when the light source is first turned on and when the patient's skin temperature is measured. For example, a period of five minutes may elapse between when the light source was first turned on and when the patient's skin temperature is taken, and the patient may then receive light-only treatment for another ten minutes.

FIGS. 14A-D illustrate thermal data on a nodal basis, according to an embodiment. In particular, FIGS. 14A-D illustrate data according to an embodiment in which the patient is exposed to both light and heat during treatment. FIG. 14A depicts a thermal map of a patient's skin or tissue temperature before heat treatment. FIG. 14B depicts a thermal map of a patient's skin or tissue temperature after heat treatment. FIG. 14C depicts temperature data, including thermocouple temperature (skin temperature) and thermistor temperature (control temperature) data at node 10, with an irradiance density of 20 mW/cm$^2$. FIG. 14D depicts a plot of temperature data over time during a ten minute soak, at 3" from the front panel (e.g., panel 10c), with a control temperature setting of 57° C.

Additional advantages and modifications will readily occur to those skilled in the art. Therefore, the present invention is not limited to the specific details and representative devices and methods, shown and described herein. Accordingly, various modifications may be made without departing from the spirit and scope of the general inventive concepts as defined by the appended claims and their equivalents.

What is claimed is:

1. A method of photodynamically diagnosing or treating a patient, comprising:
    illuminating the patient with an illuminator having a plurality of individually configurable light sources provided on a plurality of panels, the plurality of panels comprising three middle panels and two end panels, the plurality of panels being configured such that each panel of the plurality of panels is coupled to at least one other panel of the plurality of panels, wherein illuminating the patient comprises controlling the individually configurable light sources to adjust outputted power to areas on the plurality of panels;
    during the illumination, emitting heat from a heat source so as to heat the skin of the patient, wherein illumination from the plurality of light sources commences at approximately the same time as emission of heat from the heat source toward the patient, and
    controlling one or more fans mounted to one or more of the plurality of panels based on at least one of a sensed curvature of the skin of the patient or a sensed position of at least one of the plurality of panels to direct air to the skin of the patient, the fans being controllable to vary a fan speed thereof.

2. The method of claim 1, wherein controlling the individually configurable light sources comprises varying output of the plurality of light sources such that a measured output over an active emitting area is at least 60% of the measured maximum over all operation distances.

3. The method of claim 2, further comprising:
    measuring temperature at a plurality of positions within a set distance from a portion of the illuminator, and
    constructing a thermal map indicative of a temperature distribution across the plurality of positions.

4. The method of claim 1, wherein the illuminator is structured so as to surround at least three sides of the patient's head.

5. The method of claim 1, wherein the heat source is controlled so as to cause a temperature of the skin of the patient to rise by approximately 2 degrees Celsius (C) to accelerate conversion of 5-aminolevulinic acid (ALA) applied to the skin of the patient.

6. A method of photodynamically treating a patient, comprising:
    applying 5-aminolevulinic acid (ALA) to the skin of the patient to treat actinic keratosis on the extremities or torso of the patient;
    irradiating, with visible light, the skin of the patient with a plurality of light sources, each of the plurality of light sources being mounted to a panel of a five-panel illuminator, the five-panel illuminator being configured such that heat is emittable from at least a portion of one of the panels of the five-panel illuminator;
    causing air blown from at least one variable-speed fan coupled to one or more of the panels to be directed toward the skin of the patient, and controlling, via a controller, the at least one variable speed fan,
    sensing, by a sensor in communication with the controller, a configuration of the illuminator, the configuration of the illuminator corresponding to an orientation of the panels of the five-panel illuminator, and
    comparing, by the controller, an existing intensity of the light from the plurality of light sources to an intensity associated with the configuration of the illuminator and determining whether to adjust the intensity of the light sources based on the comparison.

7. The method of claim 1, wherein one of the middle panels is configurable as a center panel to oppose a face of the patient, wherein the center panel is configured to be positioned about 3 inches from the patient.

\* \* \* \* \*